(12) United States Patent
Vo et al.

(10) Patent No.: US 12,728,202 B2
(45) Date of Patent: Sep. 8, 2026

(54) MEDICATION DELIVERY PUMP FOR REDUNDANT STAGGERED GLUCOSE SENSOR INSULIN DOSAGE SYSTEM

(71) Applicant: Willow Laboratories, Inc., Irvine, CA (US)

(72) Inventors: Hung The Vo, Fountain Valley, CA (US); Sai Kong Frank Lee, Irvine, CA (US); Richard Velasco, Irvine, CA (US); Tran Minh Tuan, Irvine, CA (US)

(73) Assignee: Willow Laboratories, Inc., Irvine, CA (US)

( * ) Notice: Subject to any disclaimer, the term of this patent is extended or adjusted under 35 U.S.C. 154(b) by 997 days.

(21) Appl. No.: 17/817,613

(22) Filed: Aug. 4, 2022

(65) Prior Publication Data

US 2023/0115397 A1 Apr. 13, 2023

Related U.S. Application Data

(60) Provisional application No. 63/229,305, filed on Aug. 4, 2021.

(51) Int. Cl.

| | |
|---|---|
| ***A61M 5/172*** | (2006.01) |
| ***A61M 5/142*** | (2006.01) |
| ***A61M 5/148*** | (2006.01) |

(52) U.S. Cl.

CPC ...... *A61M 5/1723* (2013.01); *A61M 5/14244* (2013.01); *A61M 5/148* (2013.01); *A61M 2230/201* (2013.01)

(58) Field of Classification Search

None

See application file for complete search history.

(56) References Cited

U.S. PATENT DOCUMENTS

| | | | |
|---|---|---|---|
| 4,919,596 | A | 4/1990 | Slate et al. |
| 4,960,128 | A | 10/1990 | Gordon et al. |
| 4,964,408 | A | 10/1990 | Hink et al. |
| 5,319,355 | A | 6/1994 | Russek |

(Continued)

FOREIGN PATENT DOCUMENTS

| | | |
|---|---|---|
| EP | 1 874 390 | 10/2014 |
| WO | WO 2007/092618 | 8/2007 |

(Continued)

OTHER PUBLICATIONS

US 2022/0192529 A1, 06/2022, Al-Ali et al. (withdrawn)

(Continued)

*Primary Examiner* — Manuel A Mendez

(74) *Attorney, Agent, or Firm* — KNOBBE, MARTENS, OLSON & BEAR, LLP

(57) ABSTRACT

A disease management system including a medication delivery pump configured to deliver a medication from a medication pouch to a patient. The medication delivery pump may include one or more plungers configured to interrupt a flow path of medication from a medication reservoir to a patient, one or more muscle wires, and one or more disc shaped springs. The one or more muscle wires and disc shaped springs may be configured to move the one or more plungers to interrupt and uninterrupt the flow path of medication towards a patient from a medication pouch.

19 Claims, 15 Drawing Sheets

(56) References Cited

U.S. PATENT DOCUMENTS 5,325,880 A * 7/1994 Johnson .............. F16K 99/0038 60/528
5,337,744 A 8/1994 Branigan
5,341,805 A 8/1994 Stavridi et al.
D353,195 S 12/1994 Savage et al.
D353,196 S 12/1994 Savage et al.
5,377,676 A 1/1995 Vari et al.
D359,546 S 6/1995 Savage et al.
5,431,170 A 7/1995 Mathews
5,436,499 A 7/1995 Namavar et al.
D361,840 S 8/1995 Savage et al.
D362,063 S 9/1995 Savage et al.
D363,120 S 10/1995 Savage et al.
5,456,252 A 10/1995 Vari et al.
5,479,934 A 1/1996 Imran
5,482,036 A 1/1996 Diab et al.
5,494,043 A 2/1996 O'Sullivan et al.
5,533,511 A 7/1996 Kaspari et al.
5,561,275 A 10/1996 Savage et al.
5,590,649 A 1/1997 Caro et al.
5,602,924 A 2/1997 Durand et al.
5,622,482 A * 4/1997 Lee ......................... F04B 17/00 417/415
5,638,816 A 6/1997 Kiani-Azarbayjany et al.
5,638,818 A 6/1997 Diab et al.
5,645,440 A 7/1997 Tobler et al.
5,671,914 A 9/1997 Kalkhoran et al.
5,726,440 A 3/1998 Kalkhoran et al.
D393,830 S 4/1998 Tobler et al.
5,743,262 A 4/1998 Lepper, Jr. et al.
5,747,806 A 5/1998 Khalil et al.
5,750,994 A 5/1998 Schlager
5,758,644 A 6/1998 Diab et al.
5,760,910 A 6/1998 Lepper, Jr. et al.
5,890,929 A 4/1999 Mills et al.
5,919,134 A 7/1999 Diab
5,987,343 A 11/1999 Kinast
5,997,343 A 12/1999 Mills et al.
6,002,952 A 12/1999 Diab et al.
6,010,937 A 1/2000 Karam et al.
6,027,452 A 2/2000 Flaherty et al.
6,040,578 A 3/2000 Malin et al.
6,066,204 A 5/2000 Haven
6,083,248 A 7/2000 Thompson
6,115,673 A 9/2000 Malin et al.
6,124,597 A 9/2000 Shehada et al.
6,128,521 A 10/2000 Marro et al.
6,129,675 A 10/2000 Jay
6,144,868 A 11/2000 Parker
6,152,754 A 11/2000 Gerhardt et al.
6,184,521 B1 2/2001 Coffin, IV et al.
6,232,609 B1 5/2001 Snyder et al.
6,241,683 B1 6/2001 Macklem et al.
6,253,097 B1 6/2001 Aronow et al.
6,255,708 B1 7/2001 Sudharsanan et al.
6,280,381 B1 8/2001 Malin et al.
6,285,896 B1 9/2001 Tobler et al.
6,308,089 B1 10/2001 von der Ruhr et al.
6,317,627 B1 11/2001 Ennen et al.
6,321,100 B1 11/2001 Parker
6,334,065 B1 12/2001 Al-Ali et al.
6,360,114 B1 3/2002 Diab et al.
6,368,283 B1 4/2002 Xu et al.
6,375,638 B2 * 4/2002 Nason .................. A61M 5/148 604/153
6,411,373 B1 6/2002 Garside et al.
6,415,167 B1 7/2002 Blank et al.
6,423,035 B1 7/2002 Das et al.
6,427,088 B1 7/2002 Bowman et al.
6,430,437 B1 8/2002 Marro
6,430,525 B1 8/2002 Weber et al.
6,463,311 B1 10/2002 Diab
6,470,199 B1 10/2002 Kopotic et al.
6,487,429 B2 11/2002 Hockersmith et al.
6,505,059 B1 1/2003 Kollias et al.
6,525,386 B1 2/2003 Mills et al.
6,526,300 B1 2/2003 Kiani et al.
6,534,012 B1 3/2003 Hazen et al.
6,542,764 B1 4/2003 Al-Ali et al.
6,580,086 B1 6/2003 Schulz et al.
6,584,336 B1 6/2003 Ali et al.
6,587,196 B1 7/2003 Stippick et al.
6,587,199 B1 7/2003 Luu
6,595,316 B2 7/2003 Cybulski et al.
6,597,932 B2 7/2003 Tian et al.
6,606,511 B1 8/2003 Ali et al.
6,635,559 B2 10/2003 Greenwald et al.
6,639,668 B1 10/2003 Trepagnier
6,640,116 B2 10/2003 Diab
6,640,117 B2 10/2003 Makarewicz et al.
6,658,276 B2 12/2003 Kiani et al.
6,661,161 B1 12/2003 Lanzo et al.
6,697,656 B1 2/2004 Al-Ali
6,697,658 B2 2/2004 Al-Ali
RE38,476 E 3/2004 Diab et al.
RE38,492 E 4/2004 Diab et al.
6,738,652 B2 5/2004 Mattu et al.
6,760,607 B2 7/2004 Al-Ali
6,788,965 B2 9/2004 Ruchti et al.
6,816,241 B2 11/2004 Grubisic
6,822,564 B2 11/2004 Al-Ali
6,850,787 B2 2/2005 Weber et al.
6,850,788 B2 2/2005 Al-Ali
6,876,931 B2 4/2005 Lorenz et al.
6,916,159 B2 7/2005 Rush et al.
6,920,345 B2 7/2005 Al-Ali et al.
6,934,570 B2 8/2005 Kiani et al.
6,943,348 B1 9/2005 Coffin IV
6,956,649 B2 10/2005 Acosta et al.
6,961,598 B2 11/2005 Diab
6,970,792 B1 11/2005 Diab
6,985,764 B2 1/2006 Mason et al.
6,990,364 B2 1/2006 Ruchti et al.
6,998,247 B2 2/2006 Monfre et al.
7,003,338 B2 2/2006 Weber et al.
7,015,451 B2 3/2006 Dalke et al.
7,027,849 B2 4/2006 Al-Ali
D526,719 S 8/2006 Richie, Jr. et al.
7,096,052 B2 8/2006 Mason et al.
7,096,054 B2 8/2006 Abdul-Hafiz et al.
D529,616 S 10/2006 Deros et al.
7,133,710 B2 11/2006 Acosta et al.
7,142,901 B2 11/2006 Kiani et al.
7,225,006 B2 5/2007 Al-Ali et al.
RE39,672 E 6/2007 Shehada et al.
7,226,278 B2 6/2007 Nason et al.
7,254,429 B2 8/2007 Schurman et al.
7,254,431 B2 8/2007 Al-Ali et al.
7,254,434 B2 8/2007 Schulz et al.
7,274,955 B2 9/2007 Kiani et al.
D554,263 S 10/2007 Al-Ali et al.
7,280,858 B2 10/2007 Al-Ali et al.
7,289,835 B2 10/2007 Mansfield et al.
7,292,883 B2 11/2007 De Felice et al.
7,341,559 B2 3/2008 Schulz et al.
7,343,186 B2 3/2008 Lamego et al.
D566,282 S 4/2008 Al-Ali et al.
7,356,365 B2 4/2008 Schurman
7,371,981 B2 5/2008 Abdul-Hafiz
7,373,193 B2 5/2008 Al-Ali et al.
7,377,794 B2 5/2008 Al-Ali et al.
7,395,158 B2 7/2008 Monfre et al.
7,415,297 B2 8/2008 Al-Ali et al.
7,438,683 B2 10/2008 Al-Ali et al.
7,483,729 B2 1/2009 Al-Ali et al.
D587,657 S 3/2009 Al-Ali et al.
7,500,950 B2 3/2009 Al-Ali et al.
7,509,494 B2 3/2009 Al-Ali
7,510,849 B2 3/2009 Schurman et al.
7,514,725 B2 4/2009 Wojtczuk et al.
7,519,406 B2 4/2009 Blank et al.
D592,507 S 5/2009 Wachman et al.
7,530,942 B1 5/2009 Diab
7,547,281 B2 6/2009 Hayes et al.

(56) References Cited

U.S. PATENT DOCUMENTS 7,593,230 B2 9/2009 Abul-Haj et al.
7,596,398 B2 9/2009 Al-Ali et al.
7,606,608 B2 10/2009 Blank et al.
7,620,674 B2 11/2009 Ruchti et al.
D606,659 S 12/2009 Kiani et al.
7,629,039 B2 12/2009 Eckerbom et al.
7,640,140 B2 12/2009 Ruchti et al.
7,647,083 B2 1/2010 Al-Ali et al.
D609,193 S 2/2010 Al-Ali et al.
D614,305 S 4/2010 Al-Ali et al.
7,697,966 B2 4/2010 Monfre et al.
7,698,105 B2 4/2010 Ruchti et al.
RE41,317 E 5/2010 Parker
RE41,333 E 5/2010 Blank et al.
7,729,733 B2 6/2010 Al-Ali et al.
7,753,879 B2 7/2010 Mernøe
7,761,127 B2 7/2010 Al-Ali et al.
7,764,982 B2 7/2010 Dalke et al.
D621,516 S 8/2010 Kiani et al.
7,785,288 B2 8/2010 Mernøe et al.
7,791,155 B2 9/2010 Diab
RE41,912 E 11/2010 Parker
7,880,626 B2 2/2011 Al-Ali et al.
7,887,511 B2 2/2011 Mernøe et al.
7,909,772 B2 3/2011 Popov et al.
7,919,713 B2 4/2011 Al-Ali et al.
7,937,128 B2 5/2011 Al-Ali
7,937,129 B2 5/2011 Mason et al.
7,941,199 B2 5/2011 Kiani
7,957,780 B2 6/2011 Lamego et al.
7,962,188 B2 6/2011 Kiani et al.
7,976,472 B2 7/2011 Kiani
7,990,382 B2 8/2011 Kiani
7,999,674 B2 8/2011 Kamen
8,008,088 B2 8/2011 Bellott et al.
RE42,753 E 9/2011 Kiani-Azarbayjany et al.
8,028,701 B2 10/2011 Al-Ali et al.
8,048,040 B2 11/2011 Kiani
8,050,728 B2 11/2011 Al-Ali et al.
8,079,984 B2 12/2011 Rush et al.
RE43,169 E 2/2012 Parker
8,118,620 B2 2/2012 Al-Ali et al.
8,118,782 B2 2/2012 Remde
8,130,105 B2 3/2012 Al-Ali et al.
8,182,443 B1 5/2012 Kiani
8,190,223 B2 5/2012 Al-Ali et al.
8,192,394 B2 6/2012 Estes et al.
8,203,438 B2 6/2012 Kiani et al.
8,203,704 B2 6/2012 Merritt et al.
8,219,172 B2 7/2012 Schurman et al.
8,224,411 B2 7/2012 Al-Ali et al.
8,229,532 B2 7/2012 Davis
8,233,955 B2 7/2012 Al-Ali et al.
8,255,026 B1 8/2012 Al-Ali
8,265,723 B1 9/2012 McHale et al.
8,274,360 B2 9/2012 Sampath et al.
8,280,473 B2 10/2012 Al-Ali
8,294,581 B2 10/2012 Kamen
8,315,683 B2 11/2012 Al-Ali et al.
RE43,860 E 12/2012 Parker
8,346,330 B2 1/2013 Lamego
8,353,842 B2 1/2013 Al-Ali et al.
8,355,766 B2 1/2013 MacNeish, III et al.
8,374,665 B2 2/2013 Lamego
8,388,353 B2 3/2013 Kiani et al.
8,401,602 B2 3/2013 Kiani
8,414,499 B2 4/2013 Al-Ali et al.
8,414,563 B2 4/2013 Kamen et al.
8,418,524 B2 4/2013 Al-Ali
8,428,967 B2 4/2013 Olsen et al.
8,430,817 B1 4/2013 Al-Ali et al.
8,437,825 B2 5/2013 Dalvi et al.
8,455,290 B2 6/2013 Siskavich
8,457,707 B2 6/2013 Kiani
8,469,920 B2 6/2013 Mernøe et al.
8,471,713 B2 6/2013 Poeze et al.
8,473,020 B2 6/2013 Kiani et al.
8,509,867 B2 8/2013 Workman et al.
8,515,509 B2 8/2013 Bruinsma et al.
8,523,781 B2 9/2013 Al-Ali
8,527,298 B2 9/2013 Darling et al.
D692,145 S 10/2013 Al-Ali et al.
8,571,617 B2 10/2013 Reichgott et al.
8,571,618 B1 10/2013 Lamego et al.
8,571,619 B2 10/2013 Al-Ali et al.
8,577,431 B2 11/2013 Lamego et al.
8,584,345 B2 11/2013 Al-Ali et al.
8,585,377 B2 11/2013 Kamen
8,588,880 B2 11/2013 Abdul-Hafiz et al.
8,597,274 B2 12/2013 Sloan et al.
8,613,724 B2 12/2013 Lanier et al.
8,630,691 B2 1/2014 Lamego et al.
8,641,631 B2 2/2014 Sierra et al.
8,652,060 B2 2/2014 Al-Ali
8,666,468 B1 3/2014 Al-Ali
8,670,811 B2 3/2014 O'Reilly
8,679,060 B2 3/2014 Mernoe et al.
RE44,823 E 4/2014 Parker
RE44,875 E 4/2014 Kiani et al.
8,688,183 B2 4/2014 Bruinsma et al.
8,690,799 B2 4/2014 Telfort et al.
8,702,627 B2 4/2014 Telfort et al.
8,712,494 B1 4/2014 MacNeish, III et al.
8,715,206 B2 5/2014 Telfort et al.
8,723,677 B1 5/2014 Kiani
8,740,792 B1 6/2014 Kiani et al.
8,755,535 B2 6/2014 Telfort et al.
8,755,872 B1 6/2014 Marinow
8,764,671 B2 7/2014 Kiani
8,768,423 B2 7/2014 Shakespeare et al.
8,771,204 B2 7/2014 Telfort et al.
8,781,544 B2 7/2014 Al-Ali et al.
8,784,364 B2 7/2014 Kamen et al.
8,790,268 B2 7/2014 Al-Ali
8,795,233 B2 8/2014 Mernøe et al.
8,801,613 B2 8/2014 Al-Ali et al.
8,821,397 B2 9/2014 Al-Ali et al.
8,821,415 B2 9/2014 Al-Ali et al.
8,830,449 B1 9/2014 Lamego et al.
8,840,549 B2 9/2014 Al-Ali et al.
8,852,094 B2 10/2014 Al-Ali et al.
8,852,994 B2 10/2014 Wojtczuk et al.
8,897,847 B2 11/2014 Al-Ali
8,911,377 B2 12/2014 Al-Ali
8,989,831 B2 3/2015 Al-Ali et al.
8,998,809 B2 4/2015 Kiani
9,066,666 B2 6/2015 Kiani
9,066,680 B1 6/2015 Al-Ali et al.
9,095,316 B2 8/2015 Welch et al.
9,106,038 B2 8/2015 Telfort et al.
9,107,625 B2 8/2015 Telfort et al.
9,131,881 B2 9/2015 Diab et al.
9,132,227 B2 9/2015 Bryant et al.
9,138,180 B1 9/2015 Coverston et al.
9,153,112 B1 10/2015 Kiani et al.
9,180,245 B2 11/2015 Bryant et al.
9,192,329 B2 11/2015 Al-Ali
9,192,351 B1 11/2015 Telfort et al.
9,195,385 B2 11/2015 Al-Ali et al.
9,205,188 B2 12/2015 Lanigan et al.
9,211,095 B1 12/2015 Al-Ali
9,218,454 B2 12/2015 Kiani et al.
9,245,668 B1 1/2016 Vo et al.
9,267,572 B2 2/2016 Barker et al.
9,277,880 B2 3/2016 Poeze et al.
9,307,928 B1 4/2016 Al-Ali et al.
9,323,894 B2 4/2016 Kiani
D755,392 S 5/2016 Hwang et al.
9,326,712 B1 5/2016 Kiani
9,392,945 B2 7/2016 Al-Ali et al.
9,408,542 B1 8/2016 Kinast et al.
9,436,645 B2 9/2016 Al-Ali et al.
9,445,759 B1 9/2016 Lamego et al.
9,474,474 B2 10/2016 Lamego et al.

(56) References Cited

U.S. PATENT DOCUMENTS 9,480,435 B2 11/2016 Olsen
9,510,779 B2 12/2016 Poeze et al.
9,517,024 B2 12/2016 Kiani et al.
9,532,722 B2 1/2017 Lamego et al.
9,560,996 B2 2/2017 Kiani
9,579,039 B2 2/2017 Jansen et al.
9,604,001 B2 3/2017 Kamen
9,622,692 B2 4/2017 Lamego et al.
D788,312 S 5/2017 Al-Ali et al.
9,649,054 B2 5/2017 Lamego et al.
9,669,161 B2 6/2017 Bryant et al.
9,687,602 B2 6/2017 Murphy et al.
9,697,928 B2 7/2017 Al-Ali et al.
9,717,458 B2 8/2017 Lamego et al.
9,724,016 B1 8/2017 Al-Ali et al.
9,724,024 B2 8/2017 Al-Ali
9,724,025 B1 8/2017 Kiani et al.
9,737,656 B2 8/2017 Rosinko
9,749,232 B2 8/2017 Sampath et al.
9,750,442 B2 9/2017 Olsen
9,750,461 B1 9/2017 Telfort
9,750,896 B2 9/2017 Kamen et al.
9,775,545 B2 10/2017 Al-Ali et al.
9,778,079 B1 10/2017 Al-Ali et al.
9,782,077 B2 10/2017 Lamego et al.
9,787,568 B2 10/2017 Lamego et al.
9,808,188 B1 11/2017 Perea et al.
9,839,379 B2 12/2017 Al-Ali et al.
9,839,381 B1 12/2017 Weber et al.
9,847,749 B2 12/2017 Kiani et al.
9,848,800 B1 12/2017 Lee et al.
9,861,298 B2 1/2018 Eckerbom et al.
9,861,305 B1 1/2018 Weber et al.
9,877,650 B2 1/2018 Muhsin et al.
9,891,079 B2 2/2018 Dalvi
9,924,897 B1 3/2018 Abdul-Hafiz
9,931,461 B2 4/2018 Kamen et al.
9,936,917 B2 4/2018 Poeze et al.
9,955,937 B2 5/2018 Telfort
9,965,946 B2 5/2018 Al-Ali et al.
9,968,730 B2 5/2018 Blumberg et al.
D820,865 S 6/2018 Muhsin et al.
9,986,952 B2 6/2018 Dalvi et al.
D822,215 S 7/2018 Al-Ali et al.
D822,216 S 7/2018 Barker et al.
10,010,276 B2 7/2018 Al-Ali et al.
10,086,138 B1 10/2018 Novak, Jr.
10,105,286 B2 10/2018 Lanier et al.
10,111,591 B2 10/2018 Dyell et al.
D833,624 S 11/2018 DeJong et al.
10,123,729 B2 11/2018 Dyell et al.
D835,282 S 12/2018 Barker et al.
D835,283 S 12/2018 Barker et al.
D835,284 S 12/2018 Barker et al.
D835,285 S 12/2018 Barker et al.
10,149,616 B2 12/2018 Al-Ali et al.
10,154,815 B2 12/2018 Al-Ali et al.
10,159,412 B2 12/2018 Lamego et al.
10,188,348 B2 1/2019 Al-Ali et al.
RE47,218 E 2/2019 Al-Ali
RE47,244 E 2/2019 Kiani et al.
RE47,249 E 2/2019 Kiani et al.
10,195,343 B2 2/2019 Kamen et al.
10,205,291 B2 2/2019 Scruggs et al.
10,226,187 B2 3/2019 Al-Ali et al.
10,231,657 B2 3/2019 Al-Ali et al.
10,231,670 B2 3/2019 Blank et al.
10,232,113 B2 3/2019 Palerm
10,232,131 B2 3/2019 Kamen et al.
10,238,794 B2 3/2019 Kamen et al.
10,242,159 B2 3/2019 Kamen et al.
RE47,353 E 4/2019 Kiani et al.
10,279,247 B2 5/2019 Kiani
10,292,664 B2 5/2019 Al-Ali
10,299,720 B2 5/2019 Brown et al.
10,327,337 B2 6/2019 Schmidt et al.
10,327,713 B2 6/2019 Barker et al.
10,332,630 B2 6/2019 Al-Ali
10,357,606 B2 * 7/2019 Rosinko ............ A61M 5/14244
10,363,342 B2 7/2019 Dillon et al.
10,383,520 B2 8/2019 Wojtczuk et al.
10,383,527 B2 8/2019 Al-Ali
10,388,120 B2 8/2019 Muhsin et al.
D864,120 S 10/2019 Forrest et al.
10,441,181 B1 10/2019 Telfort et al.
10,441,196 B2 10/2019 Eckerbom et al.
10,448,844 B2 10/2019 Al-Ali et al.
10,448,871 B2 10/2019 Al-Ali et al.
10,456,038 B2 10/2019 Lamego et al.
10,456,090 B2 10/2019 Thorpe et al.
10,463,340 B2 11/2019 Telfort et al.
10,471,159 B1 11/2019 Lapotko et al.
10,505,311 B2 12/2019 Al-Ali et al.
10,524,738 B2 1/2020 Olsen
10,532,174 B2 1/2020 Al-Ali
10,537,285 B2 1/2020 Shreim et al.
10,542,903 B2 1/2020 Al-Ali et al.
10,555,678 B2 2/2020 Dalvi et al.
10,568,553 B2 2/2020 O'Neil et al.
10,608,817 B2 3/2020 Haider et al.
D880,477 S 4/2020 Forrest et al.
10,617,302 B2 4/2020 Al-Ali et al.
10,617,335 B2 4/2020 Al-Ali et al.
10,637,181 B2 4/2020 Al-Ali et al.
D886,849 S 6/2020 Muhsin et al.
D887,548 S 6/2020 Abdul-Hafiz et al.
D887,549 S 6/2020 Abdul-Hafiz et al.
10,667,764 B2 6/2020 Ahmed et al.
D890,708 S 7/2020 Forrest et al.
10,721,785 B2 7/2020 Al-Ali
10,736,518 B2 8/2020 Al-Ali et al.
10,750,984 B2 8/2020 Pauley et al.
D897,098 S 9/2020 Al-Ali
10,779,098 B2 9/2020 Iswanto et al.
10,827,961 B1 11/2020 Iyengar et al.
10,828,007 B1 11/2020 Telfort et al.
10,832,818 B2 11/2020 Muhsin et al.
10,849,554 B2 12/2020 Shreim et al.
10,856,750 B2 12/2020 Indorf et al.
10,874,803 B2 12/2020 Cardinali et al.
D906,970 S 1/2021 Forrest et al.
D908,213 S 1/2021 Abdul-Hafiz et al.
10,907,625 B2 2/2021 Oakes et al.
10,918,281 B2 2/2021 Al-Ali et al.
10,932,705 B2 3/2021 Muhsin et al.
10,932,729 B2 3/2021 Kiani et al.
10,939,878 B2 3/2021 Kiani et al.
10,956,950 B2 3/2021 Al-Ali et al.
D916,135 S 4/2021 Indorf et al.
D917,046 S 4/2021 Abdul-Hafiz et al.
D917,550 S 4/2021 Indorf et al.
D917,564 S 4/2021 Indorf et al.
D917,704 S 4/2021 Al-Ali et al.
10,987,066 B2 4/2021 Chandran et al.
10,991,135 B2 4/2021 Al-Ali et al.
D919,094 S 5/2021 Al-Ali et al.
D919,100 S 5/2021 Al-Ali et al.
11,000,645 B2 5/2021 Estes et al.
11,006,867 B2 5/2021 Al-Ali
D921,202 S 6/2021 Al-Ali et al.
11,024,064 B2 6/2021 Muhsin et al.
11,026,604 B2 6/2021 Chen et al.
D925,597 S 7/2021 Chandran et al.
D927,699 S 8/2021 Al-Ali et al.
11,076,777 B2 8/2021 Lee et al.
11,114,188 B2 9/2021 Poeze et al.
D933,232 S 10/2021 Al-Ali et al.
D933,233 S 10/2021 Al-Ali et al.
D933,234 S 10/2021 Al-Ali et al.
11,145,408 B2 10/2021 Sampath et al.
11,147,518 B1 10/2021 Al-Ali et al.
11,185,262 B2 11/2021 Al-Ali et al.
11,191,484 B2 12/2021 Kiani et al.
11,229,736 B2 1/2022 Cardinali et al.

(56) References Cited

U.S. PATENT DOCUMENTS 11,241,534 B2 2/2022 Miller et al.
11,246,977 B2 2/2022 Oakes et al.
D946,596 S 3/2022 Ahmed
D946,597 S 3/2022 Ahmed
D946,598 S 3/2022 Ahmed
D946,617 S 3/2022 Ahmed
11,272,839 B2 3/2022 Al-Ali et al.
11,289,199 B2 3/2022 Al-Ali
RE49,034 E 4/2022 Al-Ali
11,298,021 B2 4/2022 Muhsin et al.
D950,580 S 5/2022 Ahmed
D950,599 S 5/2022 Ahmed
D950,738 S 5/2022 Al-Ali et al.
D957,648 S 7/2022 Al-Ali
11,376,362 B2 7/2022 Mazlish
11,382,567 B2 7/2022 O'Brien et al.
11,386,482 B2 7/2022 Estes
11,389,093 B2 7/2022 Triman et al.
11,406,286 B2 8/2022 Al-Ali et al.
11,417,426 B2 8/2022 Muhsin et al.
11,439,329 B2 9/2022 Lamego
11,445,948 B2 9/2022 Scruggs et al.
11,446,435 B2 9/2022 Cardinali et al.
11,446,439 B2 9/2022 Mazlish et al.
D965,789 S 10/2022 Al-Ali et al.
D967,433 S 10/2022 Al-Ali et al.
11,464,410 B2 10/2022 Muhsin
11,504,058 B1 11/2022 Sharma et al.
11,504,066 B1 11/2022 Dalvi et al.
11,511,039 B2 11/2022 Mazlish et al.
D971,933 S 12/2022 Ahmed
D973,072 S 12/2022 Ahmed
D973,685 S 12/2022 Ahmed
D973,686 S 12/2022 Ahmed
11,529,464 B1 12/2022 Pruijs et al.
D974,193 S 1/2023 Forrest et al.
D979,516 S 2/2023 Al-Ali et al.
11,583,627 B1 2/2023 Forouzandeh et al.
D980,091 S 3/2023 Forrest et al.
11,596,363 B2 3/2023 Lamego
11,627,919 B2 4/2023 Kiani et al.
11,637,437 B2 4/2023 Al-Ali et al.
D985,498 S 5/2023 Al-Ali et al.
11,653,862 B2 5/2023 Dalvi et al.
D989,112 S 6/2023 Muhsin et al.
D989,327 S 6/2023 Al-Ali et al.
11,672,917 B2 6/2023 Cardinali et al.
11,678,829 B2 6/2023 Al-Ali et al.
11,679,579 B2 6/2023 Al-Ali
11,684,296 B2 6/2023 Vo et al.
11,684,716 B2 6/2023 Zheng et al.
11,692,934 B2 7/2023 Normand et al.
11,701,043 B2 7/2023 Al-Ali et al.
D997,365 S 8/2023 Hwang
11,721,105 B2 8/2023 Ranasinghe et al.
11,730,379 B2 8/2023 Ahmed et al.
D998,625 S 9/2023 Indorf et al.
D998,630 S 9/2023 Indorf et al.
D998,631 S 9/2023 Indorf et al.
D999,244 S 9/2023 Indorf et al.
D999,245 S 9/2023 Indorf et al.
D999,246 S 9/2023 Indorf et al.
11,766,198 B2 9/2023 Pauley et al.
D1,000,975 S 10/2023 Al-Ali et al.
11,803,623 B2 10/2023 Kiani et al.
11,832,940 B2 12/2023 Diab et al.
D1,013,179 S 1/2024 Al-Ali et al.
11,872,156 B2 1/2024 Telfort et al.
11,879,960 B2 1/2024 Ranasinghe et al.
11,883,129 B2 1/2024 Olsen
D1,022,729 S 4/2024 Forrest et al.
11,951,186 B2 4/2024 Krishnamani et al.
11,974,833 B2 5/2024 Forrest et al.
11,986,067 B2 5/2024 Al-Ali et al.
11,986,289 B2 5/2024 Dalvi et al.
11,986,305 B2 5/2024 Al-Ali et al.
D1,031,729 S 6/2024 Forrest et al.
12,004,869 B2 6/2024 Kiani et al.
12,014,328 B2 6/2024 Wachman et al.
D1,036,293 S 7/2024 Al-Ali et al.
D1,037,462 S 7/2024 Al-Ali et al.
12,029,844 B2 7/2024 Pauley et al.
12,048,534 B2 7/2024 Vo et al.
12,064,217 B2 8/2024 Ahmed et al.
12,066,426 B1 8/2024 Lapotko et al.
D1,041,511 S 9/2024 Indorf et al.
D1,042,596 S 9/2024 DeJong et al.
D1,042,852 S 9/2024 Hwang
12,076,159 B2 9/2024 Belur Nagaraj et al.
12,082,926 B2 9/2024 Sharma et al.
12,097,352 B2 9/2024 O'Connor et al.
D1,044,828 S 10/2024 Chandran et al.
D1,048,571 S 10/2024 Yu et al.
D1,048,908 S 10/2024 Al-Ali et al.
12,106,752 B2 10/2024 Campbell et al.
12,114,974 B2 10/2024 Al-Ali et al.
12,126,683 B2 10/2024 Koo et al.
12,127,838 B2 10/2024 Olsen et al.
12,128,213 B2 10/2024 Kiani et al.
12,131,661 B2 10/2024 Pauley et al.
D1,050,910 S 11/2024 Al-Ali et al.
12,178,572 B1 12/2024 Pauley et al.
12,178,581 B2 12/2024 Telfort et al.
12,178,852 B2 12/2024 Kiani et al.
D1,057,159 S 1/2025 DeJong et al.
D1,057,160 S 1/2025 DeJong et al.
12,198,790 B1 1/2025 Al-Ali
12,200,421 B2 1/2025 Campbell et al.
12,207,901 B1 1/2025 Lapotko et al.
D1,060,680 S 2/2025 Al-Ali et al.
D1,061,585 S 2/2025 Indorf
D1,063,893 S 2/2025 DeJong et al.
12,220,207 B2 2/2025 Telfort et al.
12,235,941 B2 2/2025 Kiani et al.
12,236,767 B2 2/2025 Muhsin
D1,066,244 S 3/2025 Lim et al.
D1,066,672 S 3/2025 Al-Ali et al.
12,246,160 B2 3/2025 Cardinali et al.
D1,068,656 S 4/2025 Trevisan et al.
D1,071,195 S 4/2025 Seung
D1,072,836 S 4/2025 Indorf
D1,072,837 S 4/2025 Ahmed et al.
12,272,445 B1 4/2025 Kiani
12,296,139 B2 5/2025 Estes
12,300,375 B2 5/2025 Nazzaro et al.
12,303,667 B2 5/2025 Desborough et al.
12,303,668 B2 5/2025 Mazlish et al.
D1,078,689 S 6/2025 Hwang
D1,079,020 S 6/2025 Hwang
12,336,796 B2 6/2025 Al-Ali
D1,083,653 S 7/2025 DeJong et al.
D1,085,102 S 7/2025 Indorf et al.
12,343,501 B2 7/2025 Zheng et al.
12,343,502 B2 7/2025 Mazlish et al.
12,362,596 B2 7/2025 Barker et al.
12,370,307 B2 7/2025 Lee et al.
12,370,309 B2 7/2025 Lee et al.
12,383,166 B2 8/2025 Desborough et al.
12,390,114 B2 8/2025 Novak, Jr. et al.
D1,092,244 S 9/2025 DeJong et al.
D1,093,406 S 9/2025 Indorf et al.
D1,094,735 S 9/2025 DeJong et al.
D1,095,288 S 9/2025 Lim
D1,095,483 S 9/2025 DeJong et al.
12,403,245 B2 9/2025 Estes et al.
12,403,257 B2 9/2025 Estes et al.
12,406,760 B2 9/2025 Zade et al.
12,409,270 B2 9/2025 Lee et al.
12,427,251 B2 9/2025 Lee et al.
12,429,141 B2 9/2025 McLaughlin et al.
12,431,229 B2 9/2025 Lee et al.
12,433,512 B2 10/2025 Nazzaro et al.
12,433,524 B2 10/2025 Al-Ali et al.
12,433,998 B2 10/2025 O'Connor et al.

(56) References Cited

U.S. PATENT DOCUMENTS 12,440,128 B2 10/2025 Al-Ali et al.
12,440,617 B2 10/2025 Nazzaro
D1,102,622 S 11/2025 Al-Ali et al.
12,478,272 B2 11/2025 Telfort et al.
12,478,293 B1 11/2025 Al-Ali et al.
D1,106,466 S 12/2025 Avendaño et al.
12,495,967 B2 12/2025 Muhsin et al.
12,495,999 B2 12/2025 Al-Ali et al.
12,507,952 B2 12/2025 Al-Ali et al.
12,521,021 B2 1/2026 Al-Ali et al.
12,521,506 B2 1/2026 Yu et al.
2001/0034477 A1 10/2001 Mansfield et al.
2001/0037083 A1 11/2001 Hartlaub et al.
2001/0039483 A1 11/2001 Brand et al.
2002/0010401 A1 1/2002 Bushmakin et al.
2002/0058864 A1 5/2002 Mansfield et al.
2002/0133080 A1 9/2002 Apruzzese et al.
2003/0013975 A1 1/2003 Kiani
2003/0018243 A1 1/2003 Gerhardt et al.
2003/0144582 A1 7/2003 Cohen et al.
2003/0156288 A1 8/2003 Barnum et al.
2003/0212312 A1 11/2003 Coffin, IV et al.
2004/0106163 A1 6/2004 Workman, Jr. et al.
2005/0055276 A1 3/2005 Kiani et al.
2005/0234317 A1 10/2005 Kiani
2006/0073719 A1 4/2006 Kiani
2006/0189871 A1 8/2006 Al-Ali et al.
2007/0073116 A1 3/2007 Kiani et al.
2007/0180140 A1 8/2007 Welch et al.
2007/0244377 A1 10/2007 Cozad et al.
2008/0064965 A1 3/2008 Jay et al.
2008/0094228 A1 4/2008 Welch et al.
2008/0103375 A1 5/2008 Kiani
2008/0194934 A1 8/2008 Ray et al.
2008/0221418 A1 9/2008 Al-Ali et al.
2009/0036759 A1 2/2009 Ault et al.
2009/0093687 A1 4/2009 Telfort et al.
2009/0095926 A1 4/2009 MacNeish, III
2009/0247984 A1 10/2009 Lamego et al.
2009/0275844 A1 11/2009 Al-Ali
2010/0004518 A1 1/2010 Vo et al.
2010/0030040 A1 2/2010 Poeze et al.
2010/0049132 A1 2/2010 Rush et al.
2010/0099964 A1 4/2010 O'Reilly et al.
2010/0234718 A1 9/2010 Sampath et al.
2010/0270257 A1 10/2010 Wachman et al.
2011/0028806 A1 2/2011 Merritt et al.
2011/0028809 A1 2/2011 Goodman
2011/0040197 A1 2/2011 Welch et al.
2011/0082711 A1 4/2011 Poeze et al.
2011/0087081 A1 4/2011 Kiani et al.
2011/0098548 A1 4/2011 Budiman et al.
2011/0118561 A1 5/2011 Tari et al.
2011/0137297 A1 6/2011 Kiani et al.
2011/0172498 A1 7/2011 Olsen et al.
2011/0208155 A1 8/2011 Palerm et al.
2012/0123231 A1 5/2012 O'Reilly
2012/0165629 A1 6/2012 Merritt et al.
2012/0209084 A1 8/2012 Olsen et al.
2012/0226117 A1 9/2012 Lamego et al.
2012/0283524 A1 11/2012 Kiani et al.
2013/0023775 A1 1/2013 Lamego et al.
2013/0060147 A1 3/2013 Welch et al.
2013/0096405 A1 4/2013 Garfio
2013/0296672 A1 11/2013 O'Neil et al.
2013/0345663 A1 12/2013 Agrawal et al.
2013/0345921 A1 12/2013 Al-Ali et al.
2014/0107607 A1 4/2014 Estes
2014/0166076 A1 6/2014 Kiani et al.
2014/0180160 A1 6/2014 Brown et al.
2014/0187973 A1 7/2014 Brown et al.
2014/0275871 A1 9/2014 Lamego et al.
2014/0275872 A1 9/2014 Merritt et al.
2014/0316217 A1 10/2014 Purdon et al.
2014/0316218 A1 10/2014 Purdon et al.
2014/0323897 A1 10/2014 Brown et al.
2014/0323898 A1 10/2014 Purdon et al.
2015/0005600 A1 1/2015 Blank et al.
2015/0011907 A1 1/2015 Purdon et al.
2015/0073241 A1 3/2015 Lamego
2015/0080754 A1 3/2015 Purdon et al.
2015/0099950 A1 4/2015 Al-Ali et al.
2016/0196388 A1 7/2016 Lamego
2016/0367173 A1 12/2016 Dalvi et al.
2017/0024748 A1 1/2017 Haider
2017/0173632 A1 6/2017 Al-Ali
2017/0251974 A1 9/2017 Shreim et al.
2018/0242926 A1 8/2018 Muhsin et al.
2018/0247712 A1 8/2018 Muhsin et al.
2019/0239787 A1 8/2019 Pauley et al.
2019/0320906 A1 10/2019 Olsen
2019/0374708 A1* 12/2019 Cardinali .......... A61M 5/14212
2019/0374713 A1 12/2019 Kiani et al.
2020/0060869 A1 2/2020 Telfort et al.
2020/0111552 A1 4/2020 Ahmed
2020/0113520 A1 4/2020 Abdul-Hafiz et al.
2020/0138368 A1 5/2020 Kiani et al.
2020/0163597 A1 5/2020 Dalvi et al.
2020/0196877 A1 6/2020 Vo et al.
2020/0253474 A1 8/2020 Muhsin et al.
2020/0253544 A1 8/2020 Belur Nagaraj et al.
2020/0275841 A1 9/2020 Telfort et al.
2020/0288983 A1 9/2020 Telfort et al.
2020/0321793 A1 10/2020 Al-Ali et al.
2020/0329983 A1 10/2020 Al-Ali et al.
2020/0329984 A1 10/2020 Al-Ali et al.
2020/0329993 A1 10/2020 Al-Ali et al.
2020/0330037 A1 10/2020 Al-Ali et al.
2021/0022628 A1 1/2021 Telfort et al.
2021/0104173 A1 4/2021 Pauley et al.
2021/0113121 A1 4/2021 Diab et al.
2021/0117525 A1 4/2021 Kiani et al.
2021/0118581 A1 4/2021 Kiani et al.
2021/0121582 A1 4/2021 Krishnamani et al.
2021/0154394 A1 5/2021 Larson et al.
2021/0161465 A1 6/2021 Barker et al.
2021/0236729 A1 8/2021 Kiani et al.
2021/0236730 A1 8/2021 Lee et al.
2021/0256267 A1 8/2021 Ranasinghe et al.
2021/0256835 A1 8/2021 Ranasinghe et al.
2021/0275101 A1 9/2021 Vo et al.
2021/0290060 A1 9/2021 Ahmed
2021/0290072 A1 9/2021 Forrest
2021/0290080 A1 9/2021 Ahmed
2021/0290120 A1 9/2021 Al-Ali
2021/0290177 A1 9/2021 Novak, Jr.
2021/0290184 A1 9/2021 Ahmed
2021/0296008 A1 9/2021 Novak, Jr.
2021/0330228 A1 10/2021 Olsen et al.
2021/0379282 A1 12/2021 O'Connor et al.
2021/0386382 A1 12/2021 Olsen et al.
2021/0402110 A1 12/2021 Pauley et al.
2022/0026355 A1 1/2022 Normand et al.
2022/0039707 A1 2/2022 Sharma et al.
2022/0053892 A1 2/2022 Al-Ali et al.
2022/0071562 A1 3/2022 Kiani
2022/0096603 A1 3/2022 Kiani et al.
2022/0105260 A1 4/2022 Cardinali et al.
2022/0133987 A1 5/2022 Dennis
2022/0151521 A1 5/2022 Krishnamani et al.
2022/0168500 A1 6/2022 McCaffrey
2022/0218244 A1 7/2022 Kiani et al.
2022/0218897 A1 7/2022 Nazzaro
2022/0287574 A1 9/2022 Telfort et al.
2022/0288311 A1 9/2022 Lee et al.
2022/0296161 A1 9/2022 Al-Ali et al.
2022/0323674 A1 10/2022 Kurzman et al.
2022/0339346 A1 10/2022 Stokes
2022/0361819 A1 11/2022 Al-Ali et al.
2022/0379059 A1 12/2022 Yu et al.
2022/0392610 A1 12/2022 Kiani et al.
2023/0028745 A1 1/2023 Al-Ali
2023/0038389 A1 2/2023 Vo
2023/0045647 A1 2/2023 Vo

(56) References Cited

U.S. PATENT DOCUMENTS

2023/0055226 A1 2/2023 Kamrava et al.
2023/0058052 A1 2/2023 Al-Ali
2023/0058342 A1 2/2023 Kiani
2023/0069789 A1 3/2023 Koo et al.
2023/0087671 A1 3/2023 Telfort et al.
2023/0094194 A1 3/2023 Breingan et al.
2023/0110152 A1 4/2023 Forrest et al.
2023/0111198 A1 4/2023 Yu et al.
2023/0116371 A1 4/2023 Mills et al.
2023/0117504 A1 4/2023 Kamrava et al.
2023/0122652 A1 4/2023 Breingan et al.
2023/0135297 A1 5/2023 Kiani et al.
2023/0136536 A1 5/2023 Cardinali et al.
2023/0138098 A1 5/2023 Telfort et al.
2023/0145155 A1 5/2023 Krishnamani et al.
2023/0147750 A1 5/2023 Barker et al.
2023/0210417 A1 7/2023 Al-Ali et al.
2023/0222805 A1 7/2023 Muhsin et al.
2023/0222887 A1 7/2023 Muhsin et al.
2023/0226331 A1 7/2023 Kiani et al.
2023/0233756 A1 7/2023 Lanier et al.
2023/0284916 A1 9/2023 Telfort
2023/0284943 A1 9/2023 Scruggs et al.
2023/0301562 A1 9/2023 Scruggs et al.
2023/0346993 A1 11/2023 Kiani et al.
2023/0368221 A1 11/2023 Haider
2023/0371893 A1 11/2023 Al-Ali et al.
2023/0389837 A1 12/2023 Krishnamani et al.
2024/0016418 A1 1/2024 Devadoss et al.
2024/0016419 A1 1/2024 Devadoss et al.
2024/0047061 A1 2/2024 Al-Ali et al.
2024/0049310 A1 2/2024 Al-Ali et al.
2024/0049986 A1 2/2024 Al-Ali et al.
2024/0081656 A1 3/2024 DeJong et al.
2024/0122486 A1 4/2024 Kiani
2024/0180456 A1 6/2024 Al-Ali
2024/0188872 A1 6/2024 Al-Ali et al.
2024/0197984 A1 6/2024 Murphy et al.
2024/0234066 A9 7/2024 Wiel et al.
2024/0245855 A1 7/2024 Vo et al.
2024/0260894 A1 8/2024 Olsen
2024/0267698 A1 8/2024 Telfort et al.
2024/0277233 A1 8/2024 Al-Ali
2024/0277280 A1 8/2024 Al-Ali
2024/0298920 A1 9/2024 Fernkbist et al.
2024/0306985 A1 9/2024 Vo et al.
2024/0324953 A1 10/2024 Telfort
2024/0380246 A1 11/2024 Moran
2024/0380247 A1 11/2024 Moran
2024/0404549 A1 12/2024 Campbell et al.
2025/0000458 A1 1/2025 Abdul-Hafiz et al.
2025/0037836 A1 1/2025 Kiani
2025/0100482 A1 3/2025 Al-Ali et al.
2025/0118415 A1 4/2025 Olsen
2025/0135114 A1 5/2025 Bussiere et al.
2025/0144295 A1 5/2025 Zheng et al.
2025/0205427 A1 6/2025 Lee et al.
2025/0246285 A1 7/2025 Alles et al.
2025/0255764 A1 8/2025 Stead
2025/0278512 A1 9/2025 Koo et al.
2025/0281059 A1 9/2025 Avendano
2025/0281078 A1 9/2025 Desborough et al.
2025/0281688 A1 9/2025 Estes
2025/0288250 A1 9/2025 Al-Ali et al.
2025/0295366 A1 9/2025 Al-Ali et al.
2025/0302426 A1 10/2025 Ha et al.
2025/0311949 A1 10/2025 Al-Ali et al.
2025/0318761 A1 10/2025 Al-Ali et al.
2025/0319257 A1 10/2025 Mazlish et al.
2025/0322950 A1 10/2025 Al-Ali et al.
2025/0323417 A1 10/2025 Rey
2025/0329240 A1 10/2025 Kiani
2025/0344010 A1 11/2025 Al-Ali et al.
2026/0014333 A1 1/2026 Fernkvist et al.
2026/0014334 A1 1/2026 Danwihl

FOREIGN PATENT DOCUMENTS

WO WO-2011082272 A2 * 7/2011 .............. A61M 5/36
WO WO 2018/115884 6/2018
WO WO 2018/146467 8/2018
WO WO 2023/014914 2/2023
WO WO 2023/241918 12/2023

OTHER PUBLICATIONS

US 2024/0016391 A1, 01/2024, Lapotko et al. (withdrawn)

Invitation to Pay Additional Fees received in PCT Application No. PCT/US2022/039477 as mailed Dec. 15, 2022 in 12 pages.

International Search Report and Written Opinion received in PCT Application No. PCT/US2022/039477 as mailed Feb. 6, 2023 in 18 pages.

Ellingsen et al., "Safety Constraints in an Artificial Pancreatic β Cell: An Implementation of Model Predictive Control with Insulin on Board", Journal of Diabetes Science and Technology, vol. 3, No. 3, May 2009, pp. 536-544.

Invitation to Pay Additional Fees received in PCT Application No. PCT/US2025/041702 as mailed Nov. 14, 2025 in 19 pages.

International Search Report and Written Opinion received in PCT Application No. PCT/US2025/04170 as mailed Jan. 9, 2026 in 23 pages.

* cited by examiner

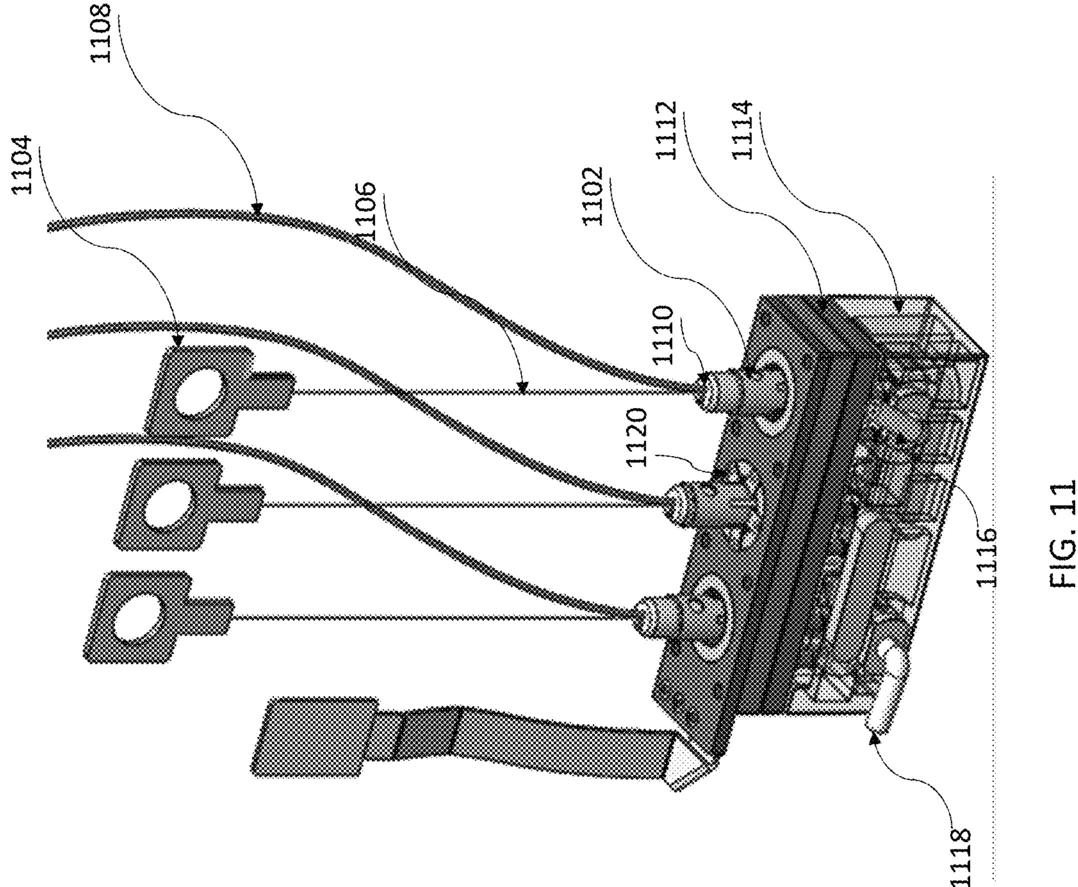
FIG. 11
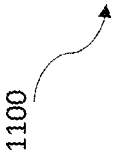

MEDICATION DELIVERY PUMP FOR REDUNDANT STAGGERED GLUCOSE SENSOR INSULIN DOSAGE SYSTEM

BACKGROUND

Field of the Invention

The general field of this disclosure is glucose sensing and disease management systems.

Description of the Related Art

Diabetes is a chronic disease that impacts many individuals, both adults and children. The management of diabetes may include the measurement of glucose within the interstitial space including blood and/or interstitial fluid of a patient and administration of insulin to the patient. A closed loop insulin administration system includes both a sensor to take glucose measurements from the interstitial space including blood and/or interstitial fluid of the patient and an insulin administration device which administers insulin to the patient based on the glucose measurements. Closed loop insulin administration systems allow individuals impacted by diabetes to go about daily life with much less worry about their insulin or glucose levels which can vastly improve a diabetic's quality of life.

SUMMARY

Various aspects of systems, methods and devices within the scope of the appended claims each have several aspects, no single one of which is solely responsible for the desirable attributes described herein. Without limiting the scope of the appended claims, some prominent features are described herein.

A disease management device can include a patch or a patient worn insulin pump. In some aspects, the pump can be configured to be lightweight and compact. For example, the pump can be configured to have a small area and occupy and minimal footprint within the device. Similarly, the pump can be lightweight to minimize the weight of the device. In some aspects, the device can be configured to operate with low or ultra-low power. In some aspects, the pump can operate on a per cycle basis, which can decrease the speed of the pump and/or maximize the precision and accuracy of the pump. Similarly, the pump can be configured to emit a minimal amount of energy or heat, which can increase the efficiency of the pump and the device.

A disease management device can include: a medication delivery pump configured to deliver a medication from a medication pouch to a patient, the medication delivery pump can include: one or more blockers, also referred to herein as plungers or pistons, configured to interrupt a flow path of medication from a medication reservoir to a patient when in an uncontracted position; one or more wires, such as muscle wire, operably connected to the one or more blockers, wherein when the one or more wires are contracted, at least one blocker of the one or more blockers is configured to open the flow path of medication. The disease management device can also include one or more springs configured to provide retraction pressure on at least one of the one or more blockers such that when a coupled wire is not contracted, the one or more blockers is retracted to an uncontracted position and interrupts the flow path of medication. The muscle wire can include nitonol wire which can contract itself when electricity is applied. The one or more springs can include one or more disc shaped springs. The one or more springs can include silicon.

The device can include an analyte sensor. The medication can include at least one of insulin or glucagon or any other administrable medication. The one or more blockers can include a first, second, and third blocker configured to interrupt the flow path of medication in a first, second, and third portion of the flow path respectively. The one or more hardware processors can be configured to cause one or more muscle wires to engage the first, second, and third blocker in a pattern to cause medication to move from the medication pouch to the patient through the flow path. To engage the first, second, and third blocker in a pattern, the one or more hardware processors can be configured to: apply a first electric signal to a first muscle wire to cause the first muscle wire to cause the first blocker to open the flow path in the first portion; cease applying the first electrical signal to the first muscle wire in order to allow a first spring to apply retraction pressure to the first blocker such that the first blocker is retracted to an uncontracted position and interrupts the flow path in the first portion; apply a second electrical signal to a second muscle wire to cause the second blocker to open the flow path in the second portion; cease applying the second electrical signal to the second muscle wire in order to allow a second spring to apply retraction pressure to the second blocker such that the second blocker is retracted to an uncontracted position and interrupts the flow path in the second portion; and apply a third electrical signal to a third muscle wire of the one or more muscle wires to cause the third blocker to open the flow path in the third portion.

In certain aspects, a disease management device comprises: a medication delivery pump configured to deliver a medication from a medication pouch to a patient, the medication delivery pump comprising: one or more blockers configured to interrupt a flow path of medication from a medication reservoir to a patient when in a first position; and one or more wires operably connected to the one or more blockers, wherein when the one or more wires are activated, at least one blocker of the one or more blockers is configured to open the flow path of medication.

In certain aspects, the device further comprises one or more springs configured to provide retraction pressure on at least one of the one or more blockers such that when a coupled wire is not activated, the one or more blockers is positioned to interrupt the flow path of medication.

In certain aspects, the one or more blockers are one or more plungers.

In certain aspects, the one or more wires are one or more muscle wires which expand or contract when electricity is applied to the one or more muscle wires.

In certain aspects, the blockers block the flow of medication when the one or more wires are not activated.

In certain aspects, the disease management device comprises an analyte sensor.

In certain aspects, the medication comprises at least one of insulin or glucagon.

In certain aspects, the one or more springs comprise disc shaped springs.

In certain aspects, the one or more springs comprise silicon.

In certain aspects, the one or more muscle wires comprise nitonol wire.

In certain aspects, the one or more muscle wires comprise a nickel titanium alloy.

In certain aspects, the one or more blockers comprise a first, second, and third blocker configured to interrupt the flow path of medication in a first, second, and third location of the flow path respectively.

In certain aspects the disease management system comprises one or more hardware processors configured to cause the one or more wires to activate and engage at least one of the one or more blockers in a pattern to cause medication to move from the medication pouch to the patient.

In certain aspects, the one or more hardware processors are configured to activate a first, and second blockers in a pattern, wherein the one or more hardware processors are configured to: apply a first electrical signal to a first wire to cause the first wire to cause the first blocker to open the flow path in a first portion cease applying the first electrical signal to the first wire in order to allow a first spring to apply retraction pressure to the first blocker such that the first blocker is retracted to an uncontracted position and interrupts the flow path in a first portion; apply a second electrical signal to a second wire to cause the second blocker to open the flow path in a second portion; and cease applying the second electrical signal to the second wire in order to allow a second spring to apply retraction pressure to the second blocker such that the second blocker is retracted to an uncontracted position and interrupts the flow path in the second portion.

In certain aspects, the one or more hardware processors are configured to activate a first, second, and third blockers in a pattern, wherein the one or more hardware processors are configured to: apply a first electrical signal to a first wire to cause the first wire to cause the first blocker to open the flow path in a first portion; cease applying the first electrical signal to the first wire in order to allow a first spring to apply retraction pressure to the first blocker such that the first blocker is retracted to an uncontracted position and interrupts the flow path in a first portion; apply a second electrical signal to a second wire to cause the second blocker to open the flow path in a second portion; cease applying the second electrical signal to the second wire in order to allow a second spring to apply retraction pressure to the second blocker such that the second blocker is retracted to an uncontracted position and interrupts the flow path in the second portion; and apply a third electrical signal to a third wire of the one or more wires to cause the third blocker to open the flow path in a third portion.

In certain aspects, the one or more blockers are configured to substantially or partially block the flow path of medication.

In certain aspects, the medication delivery pump further comprises a feedback control system.

In certain aspects, the disease management system performs a method to pump liquid medication from a medication pouch to a patient, the method comprising: interrupting a flow path of liquid medication from a liquid medication reservoir to the patient when one or more blockers is in an uncontracted position; and contracting the one or more blockers to open at least part of the flow path.

In certain aspects the disease management system provides retraction pressure by one or more springs on at least one of the one or more blockers to retract the one or more blockers to an uncontracted position and interrupt the flow path of liquid medication In certain aspects, the performed method further comprises sensing one or more physiological parameters of a patient with an analyte sensor.

In certain aspects, the performed method further comprises comprising sensing one or more physiological parameters of a patient with an analyte sensor.

In certain aspects, the liquid medication includes at least one of insulin or glucagon.

In certain aspects, the one or more springs include silicon.

In certain aspects, the one or more blockers comprise one or more plungers.

In certain aspects, contracting the one or more blockers comprises using muscle wire to contract the one or more blockers.

In certain aspects, the one or more muscle wires include nitinol wire.

In certain aspects, the one or more blockers include a first, second, and third blocker configured to interrupt the flow path of liquid medication in a first, second, and third portion of the flow path respectively.

In certain aspects the disease management system comprises one or more hardware processors causing one or more muscle wires to engage first, second, and third blocker in a pattern to cause the liquid medication to flow from the medication pouch to the patient.

In certain aspects, the method performed further comprises: applying a first electrical signal to a first muscle wire to cause the first muscle wire to cause the first blocker to open the flow path in a first portion; ceasing applying the first electrical signal to the first muscle wire in order to allow a first spring to apply retraction pressure to the first blocker such that the first blocker is retracted to an uncontracted position and interrupts the flow path in the first portion; applying a second electrical signal to a second muscle wire to cause the second blocker to open the flow path in a second portion; ceasing applying the second electrical signal to the second muscle wire in order to allow a second spring to apply retraction pressure to the second blocker such that the second blocker is retracted to an uncontracted position and interrupts the flow path in the second portion; and applying a third electrical signal to a third muscle wire of the one or more muscle wires to cause the third blocker to open the flow path in a third portion.

In certain aspects, a method to engage a system of blockers configured to interrupt a flow path of liquid medication from a medication reservoir to a patient is performed, the method comprising: applying a first electrical signal to a first muscle wire to cause the first muscle wire to cause a first blocker to open the flow path in a first portion of the flow path; ceasing applying the first electrical signal to the first muscle wire in order to allow a first spring to apply retraction pressure to the first blocker such that the first blocker is retracted to an uncontracted position and interrupts the flow path in the first portion of the flow path; applying a second electrical signal to a second muscle wire to cause the second blocker to open the flow path in a second portion of the flow path; ceasing applying the second electrical signal to the second muscle wire in order to allow a second spring to apply retraction pressure to the second blocker such that the second blocker is retracted to an uncontracted position and interrupts the flow path in the second portion; and applying a third electrical signal to a third muscle wire to cause the third blocker to open the flow path in a third portion.

In certain aspects, a muscle wire pump system configured to manage a liquid medication flow path is provided. The system comprising: a controller configured to control operation of a pump by operating at least one blocker within the liquid medication flow path; and one or more muscle wires coupled to at least one of the at least one blocker and configured to receive an electrical signal and cause contraction of at least one of the at least one blocker to retract the at least one blocker to allow an uninterrupted liquid medical flow path.

In certain aspects, the muscle wire pump comprises one or more springs coupled to a plate forming an assembly with the at least one blocker.

In certain aspects, the plate includes one or more holes configured to allow the one or more holes to receive at least a portion of the at least one blocker.

In certain aspects, the one or more springs comprises disc springs.

In certain aspects, a method to engage a system of blockers configured to interrupt a flow path of liquid medication from a medication reservoir to a patient is provided. The method comprising: applying a first electrical signal to a first muscle wire to cause the first muscle wire to cause a first blocker to open the flow path in a first portion of the flow path; ceasing applying the first electrical signal to the first muscle wire in order to allow a first spring to apply retraction pressure to the first blocker such that the first blocker is retracted to an uncontracted position and interrupts the flow path in the first portion of the flow path; and applying a second electrical signal to a second muscle wire to cause the second blocker to open the flow path in a second portion of the flow path.

In certain aspects, a method to monitor a device with a feedback mechanism, the method comprising: connecting a conductive wire to a component of the device and a feedback contact portion; triggering a signal when the feedback contact portion contacts a feedback layer; analyzing the signal; and controlling the device based on an analysis of the signal.

In certain aspects. the signal includes a status the component of the device.

In certain aspects, a disease management device comprising: a medication delivery pump configured to deliver a medication from a medication pouch to a patient, the medication delivery pump comprising: at least two pistons configured pump medication from a medication reservoir to a patient; and at least two wires, at least one wire operably connected to each one of the at least two pistons, wherein when the one or more wires are activated, at least one piston of the one or more pistons is configured to open the flow path of medication and create negative pressure to draw medication into the flow path.

In certain aspects the device further comprising two or more springs configured to provide retraction pressure on at least one of the at least two or more pistons such that when a coupled wire is not activated, the one or more pistons is repositioned to apply positive pressure on the medication and interrupt the flow path of medication once fully unretracted.

In certain aspects, the one or more pistons are one or more plungers.

In certain aspects, the one or more wires are one or more muscle wires which expand or contract when electricity is applied to the one or more muscle wires.

In certain aspects, the pistons block the flow of medication when the one or more wires are not activated.

In certain aspects, the device further comprising an analyte sensor.

In certain aspects, the medication comprises at least one of insulin or glucagon.

In certain aspects, the one or more springs comprise disc shaped springs.

In certain aspects, the one or more springs comprise silicon.

In certain aspects, the one or more muscle wires comprise nitinol wire.

In certain aspects, the one or more muscle wires comprise a nickel titanium alloy.

In certain aspects, the at least two pistons comprise a first, second, and third piston configured to interrupt the flow path of medication in a first, second, and third location of the flow path respectively.

In certain aspects, the device further comprising one or more hardware processors configured to cause the two or more wires to activate and engage at least one of the at least two or more pistons in a pattern to cause medication to move from the medication pouch to the patient.

In certain aspects, the one or more hardware processors are configured to activate a first, and second pistons in a pattern, wherein the one or more hardware processors are configured to: apply an electrical signal to a first wire and a second wire to cause the first wire to cause the first piston to open the flow path in a first portion and the second wire to cause the second piston to open the flow path in a second portion substantially simultaneously, the first and second pistons generating negative pressure configured to draw medication in the flow path; and cease applying the electrical signal to the first wire in order to allow a first spring to apply retraction pressure to the first piston such that the first piston is retracted to an uncontracted position and interrupts the flow path in the first portion.

In certain aspects, the one or more hardware processors are configured to activate a first, second, and third pistons in a pattern, wherein the one or more hardware processors are configured to: apply an electrical signal to a first wire and a second wire to cause the first wire to cause the first piston to open the flow path and create negative pressure in a first position and the second wire to cause the second piston to open the flow path and create negative pressure in a second position substantially simultaneously; cease applying the electrical signal to the first wire in order to allow a first spring to apply retraction pressure to the first piston such that the first piston is retracted to an uncontracted position and interrupts the flow path in a first portion; and apply a second electrical signal to a third wire to cause the third piston to open the flow path in a third position and cease applying the electrical signal to the second wire at substantially the same time in order to allow a second spring to apply retraction pressure to the second piston such that the second piston is retracted to an uncontracted position and applies positive pressure to the medication and interrupts the flow path in a second portion.

In certain aspects, the one or more pistons are configured to substantially or partially block the flow path of medication.

In certain aspects, the medication delivery pump further comprises a feedback control system.

In certain aspects, a method to pump liquid medication from a medication pouch to a patient, the method comprising: interrupting a flow path of liquid medication from a liquid medication reservoir to the patient when one or more pistons is in an uncontracted position; and contracting the one or more pistons to open at least part of the flow path and generate negative pressure to draw medication into the flow path.

In certain aspects, the method further comprising providing retraction pressure by one or more springs on at least one of the one or more pistons to retract the one or more pistons to an uncontracted position and interrupt the flow path of liquid medication and apply positive pressure to the medication in the flow path.

In certain aspects, the method further comprising sensing one or more physiological parameters of a patient with an analyte sensor.

In certain aspects, the method further comprising sensing one or more physiological parameters of a patient with an analyte sensor.

In certain aspects, the liquid medication includes at least one of insulin or glucagon.

In certain aspects, the one or more springs include silicon.

In certain aspects, the one or more pistons comprise one or more plungers.

In certain aspects, contracting the one or more pistons comprises using muscle wire to contract the one or more pistons.

In certain aspects, the one or more muscle wires include nitinol wire.

In certain aspects, the one or more pistons include a first, second, and third piston configured to interrupt the flow path of liquid medication in a first, second, and third portion of the flow path respectively.

In certain aspects, the method further comprising one or more hardware processors causing one or more muscle wires to engage first, second, and third piston in a pattern to cause the liquid medication to flow from the medication pouch to the patient.

In certain aspects, the method further comprising: applying an electrical signal to a first wire and a second wire to cause the first wire to cause the first piston to open the flow path and create negative pressure to cause medication to flow into the flow path in a first portion and the second wire to cause the second piston to open the flow path in a second portion; ceasing applying the electrical signal to the first wire in order to allow a first spring to apply retraction pressure to the first piston such that the first piston is retracted to an uncontracted position and causes positive pressure to be applied to the medication and interrupts the flow path in the first portion; and applying a second electrical signal to a third wire to cause the third piston to open the flow path in a third portion and cease applying the electrical signal to the second wire in order to allow a second spring to apply retraction pressure to the second piston such that the second piston is retracted to an uncontracted position and applies positive pressure to the medication in the flow path and interrupts the flow path in the second portion.

In certain aspects, a method to engage a system of pistons configured to pump medication to a patient and interrupt a flow path of liquid medication from a medication reservoir to a patient, the method comprising: applying an electrical signal to a first wire and a second wire to cause the first wire to cause the first piston to open the flow path in a first portion and the second wire to cause the second piston to open the flow path in a second portion at substantially simultaneously; ceasing applying the electrical signal to the first wire in order to allow a first spring to apply retraction pressure to the first piston such that the first piston is retracted to an uncontracted position and interrupts the flow path in the first portion; and applying a second electrical signal to a third wire to cause the third piston to open the flow path in a third portion and cease applying the electrical signal to the second wire substantially simultaneously in order to allow a second spring to apply retraction pressure to the second piston such that the second piston is retracted to an uncontracted position and interrupts the flow path in the second portion.

In certain aspects, a muscle wire pump system configured to manage a liquid medication flow path, the system comprising: a controller configured to control operation of a pump by operating at least one piston within the liquid medication flow path; and one or more muscle wires coupled to at least one of the at least one piston and configured to receive an electrical signal and cause contraction of at least one of the at least one piston to retract the at least one piston to allow an uninterrupted liquid medical flow path and create negative pressure to draw medication into the flow path.

In certain aspects, the muscle wire pump system further comprising one or more springs coupled to a plate forming an assembly with the at least one piston.

In certain aspects, the plate includes one or more holes configured to allow the one or more holes to receive at least a portion of the at least one piston.

In certain aspects, the one or more springs comprises disc springs.

In certain aspects, a method to engage a system of pistons configured to interrupt a flow path of liquid medication from a medication reservoir to a patient, the method comprising: applying an electrical signal to a first wire and a second wire to cause the first wire to cause the first piston to open the flow path in a first portion and the second wire to cause the second piston to open the flow path in a second portion substantially simultaneously and create negative pressure to draw medication in to the flow path; and ceasing applying the electrical signal to the first wire in order to allow a first spring to apply retraction pressure to the first piston such that the first piston is retracted to an uncontracted position and interrupts the flow path in the first portion.

BRIEF DESCRIPTION OF THE DRAWINGS

These and other sample aspects of the disclosure will be described in the detailed description and the appended claims that follow, and in the accompanying drawings.

FIG. 11 illustrates an example muscle wire pump that includes a feedback control system.

Figure 1:
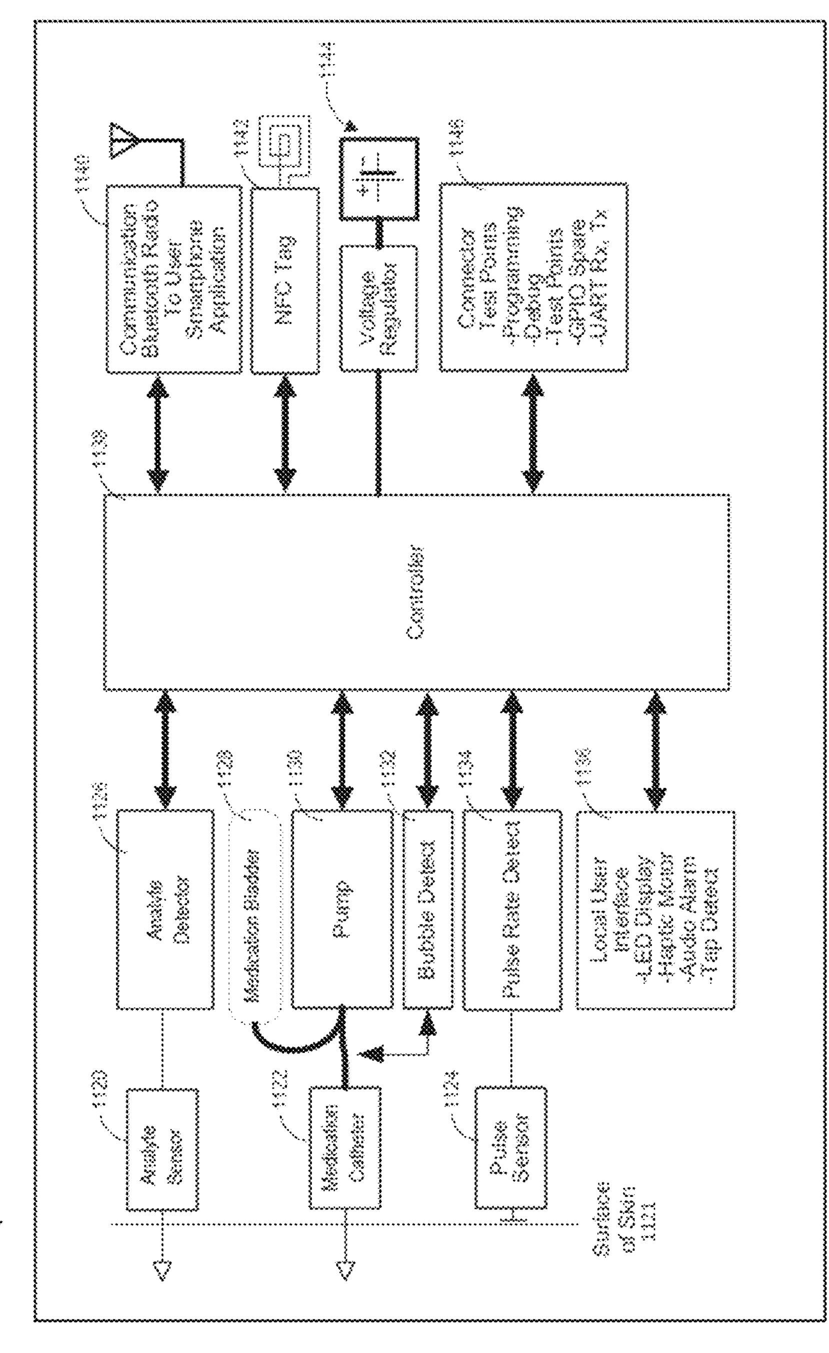
FIG. 1 illustrates an example disease management system that may be part of a disease management environment or used as an interleaved device.

In accordance with common practice the various features illustrated in the drawings may not be drawn to scale. Accordingly, the dimensions of the various features may be arbitrarily expanded or reduced for clarity. In addition, some of the drawings may be simplified for clarity. Thus, the drawings may not depict all of the components of a given apparatus (e.g., device) or method. Finally, like reference numerals may be used to denote like features throughout the specification and figures.

DETAILED DESCRIPTION

Although certain preferred aspects and examples are disclosed below, inventive subject matter extends beyond the specifically disclosed aspects to other alternative aspects and/or uses and to modifications and equivalents thereof. Thus, the scope of the claims that may arise here from is not limited by any of the particular aspects described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain aspects; however, the order of description should not be construed to imply that these operations are order dependent. Additionally, the structures, systems, and/or devices described herein may be embodied as integrated components or as separate components. For purposes of comparing various aspects, certain aspects and advantages of these aspects are described. Not necessarily all such aspects or advantages are achieved by any particular aspect. Thus, for example, various aspects may be carried out in a manner that achieves or optimizes one advantage or group of advantages as taught herein without necessarily achieving other aspects or advantages as may also be taught or suggested herein.

A. Example Disease Management System

FIG. 1 shows a block diagram of an example disease management system 1101. In some examples, the disease management system 1101 may be part of a disease management environment, such as described above. A disease management system 1101 may be configured to measure one or more physiological parameters of a patient (such as pulse, skin temperature, or other values), measure one or more analytes present in the blood of a patient (such as glucose, lipids, or other analyte) and administer medication (such as insulin, glucagon, or other medication). In some examples, a disease management system 1101 may be configured to communicate with one or more hardware processors that may be external to the disease management system 1101, such as a cloud-based processor or user device. A disease management system 1101 may include an NFC tag to support authentication and pairing with a user device (for example, smart phone or smart watch), Bluetooth communication with additional disease management systems or devices, and Bluetooth communication with a paired user device running an associated control application. To support ease of use and safe interaction with the patient, the system may incorporate user input through a tap-detecting accelerometer and provide feedback via an audio speaker, haptic vibration, and/or optical indicators. The system may operate on battery power and support both shelf-life and reliable operation once applied to the patient. Battery life may be managed through control of several planned levels of sleep and power consumption. To support this reliability, a controller can monitor several system-health parameters, and monitor temperatures of the included medication, and ambient temperature for the life of the device.

As illustrated in FIG. 1, a controller 1138 of the disease management system 1101 may be configured to communicate and control one or more components of the disease management system 1101. The controller 1138 may include one or more hardware processors, such as a printed circuit board (PCB) or the like. The controller 1138 may be configured to communicate with peripheral devices or components to support the accurate measurement of physiological parameters and blood analytes, such as patient pulse, temperature, and blood glucose, using detector electronics. The controller 1138 may subsequently calculate dose or receive a calculated dose value and administer medication, such as insulin, by actuation of an actuated pump. The controller 1138 may record device activity and transfer the recorded data to non-volatile secure memory space. At the end of the life of a device or system, the controller can be configured to lock operation, and create a data recovery module to permit authenticated access to the recorded data if needed.

A disease management system 1101 may include an analyte sensor 1120. The analyte sensor 1120 may be configured to detect analytes in the patient's blood. For example, an analyte sensor 1120 can include a glucose sensing probe configured to pierce the surface of the skin 1121. In some examples, a disease management system 1101 may include a plurality of analyte sensors 1120 to detect one or more analytes. In some examples, an analyte sensor 1120 may be configured to detect a plurality of analytes. Sensed analytes may include, but are not limited to, glucose, insulin, and other analytes. An analyte sensor 1120 may be configured to communicate with an analyte detector 1126. The analyte detector 1126 may be configured to receive a signal of one or more analyte sensors 1120 in order to measure one or more analytes in the blood of the patient. The analyte detector 1126 may be configured to communicate with the controller 1138. For example, the analyte detector 1126 may be configured to, for example, send analyte values to the controller 1138 and receive control signals from the controller.

A disease management system 1101 may include a medication catheter 1122. The medication catheter 1122 may be configured to administer medication, including, but not limited to insulin, to the patient. The medication catheter 1122 may receive medication from a medication bladder 1128 configured to contain medication to be administered. The medication bladder 1128 may be configured to contain medication for a prolonged period, such as 1 day, 3 days, 6 days, or more. The medication bladder 1128 may be configured to contain certain medication types, such as insulin. In some examples, a disease management system 1101 may include a plurality of medication bladders 1128 for one or more reservoirs of the same or different medications. In some examples, a disease management system 1101 may be configured to mix medications from medication bladders 1128 prior to administration to the patient. A pump 1130 may be configured to cause medication to be administered from the bladder 1128 to the patient through the insulin catheter 1122. A pump 1130 may include, but is not limited to, a pump such as described herein.

A disease management system 1101 may optionally include a physiological sensor 1124. The physiological sensor 1124 may include a pulse rate sensor, temperature sensor, pulse oximeter, the like or a combination thereof. In some examples, a disease management system 1101 may be configured to include a plurality of physiological sensors. The physiological sensor 1124 may be configured to communicate with a physiological detector 1134. The physiological detector 1134 may be configured to receive a signals of the physiological sensor 1124. The physiological detector 1134 may be configured to measure or determine and communicate a physiological value from the signal. The physiological detector 1134 may be configured to communicate with the controller 1138. For example, the physiological detector 1134 may be configured to, for example, send measured physiological values to the controller 1138 and receive control signals from the controller.

A disease management system 1101 may include one or more local user interfacing components 1136. For example, a local user interfacing component 1136 may include, but is not limited to one or more optical displays, haptic motors, audio speakers, and user input detectors. In some examples, an optical display may include an LED light configured to display a plurality of colors. In some examples, an optical display may include a digital display of information associated with the disease management system 1101, including, but not limited to, device status, medication status, patient status, measured analyte or physiological values, the like or a combination thereof. In some examples, a user input detector may include an inertial measurement unit, tap detector, touch display, or other component configured to accept and receive user input. In some examples, audio speakers may be configured to communicate audible alarms related to device status, medication status user status, the like or a combination thereof. A controller 1138 may be configured to communicate with the one or more local interfacing components 1136 by, for example, receiving user input from the one or more user input components or sending control signals to, for example, activate a haptic motor, generate an output to the optical display, generate an audible output, or otherwise control one or more of the local user interfacing components 1136.

A disease management system 1101 may include one or more communication components 1140. A communication component 1140 can include but is not limited to one or more radios configured to emit Bluetooth, cellular, Wi-Fi, or other wireless signals. In some examples, a communication component 1140 can include a port for a wired connection. Additionally, a disease management system 1101 may include an NFC tag 1142 to facilitate in communicating with one or more hardware processors. The one or more communication components 1140 and NFC tag 1142 may be configured to communicate with the controller 1138 in order to send and/or receive information associated with the disease management system 1101. For example, a controller 1138 may communicate medication information and measured values through the one or more communication components 1140 to an external device. Additionally, the controller 1138 may receive instructions associated with measurement sampling rates, medication delivery, or other information associated with operation of the management system 1101 through the one or more communication components 1140 from one or more external devices.

A disease management system 1101 may include one or more power components 1144. The power components may include but are not limited to one or more batteries and power management components, such as a voltage regulator. Power from the one or more power components 1144 may be accessed by the controller and/or other components of the disease management system 1101 to operate the disease management system 1101.

A disease management system 1101 may have one or more power and sleep modes to help regulate power usage. For example, a disease management system 1101 may have a sleep mode. The sleep mode may be a very low power mode with minimal functions, such as the RTC (or real time clock) and alarms to wake the system and take a temperature measurement of the system, or the like. In another example, a disease management system 1101 may include a measure temperature mode which may correspond to a low power mode with reduced functions. The measure temperature mode may be triggered by the RTC where the system is configured to take a temperature measurement, save the value, and return the system to a sleep mode. In another example, a disease management system 1101 may include a wake-up mode. The wake-up mode may be triggered by an NFC device and allow the system to pair with an external device with, for example, Bluetooth. If a pairing event does not occur, the system may return to sleep mode. In another example, a disease management system 1101 may include a pairing mode. The pairing mode may be triggered by an NFC device. When a controlling application is recognized, the system may proceed to pair with the application and set the system to an on condition and communicate to the cloud or other external device to establish initial data movement. In another example, a disease management system 1101 may include a rest mode where the system is configured to enter a lower power mode between measurements. In another example, a disease management system 1101 may include a data acquisition mode where the system is configured to enter a medium power mode where data acquisition takes place. In another example, a disease management system 1101 may include a parameter calculation mode where the system is configured to enter a medium power mode where parameter calculations, such as a blood glucose calculation, are performed and data is communicated to an external device and/or the cloud. In another example, a disease management system 1101 may include a pump mode where the system is configured to enter a higher power mode where the pump draws power to deliver medication to the patient.

A disease management system 1101 may include one or more connector test points 1146. The connecter test points may be configured to aid in programming, debugging, testing or other accessing of the disease management system 1101. In some examples, connector test points 1146 may include, for example, a GPIO spare, UART receiver or transmitter, the like or a combination thereof.

Figure 2:
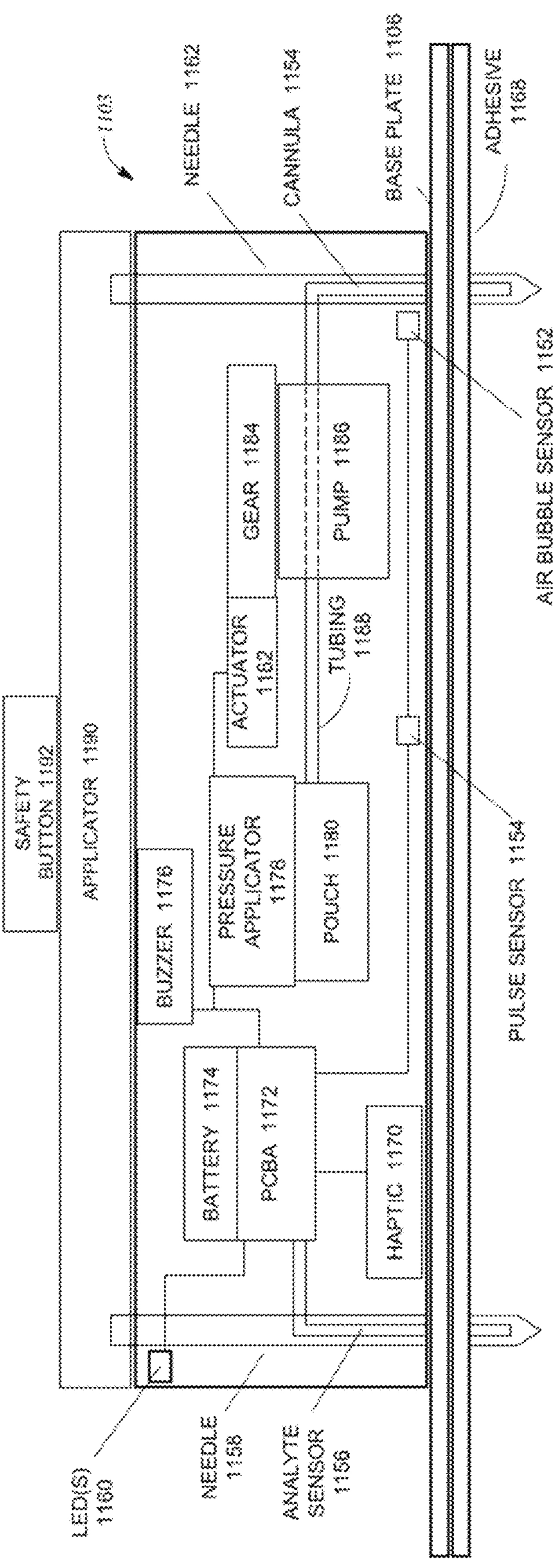
FIG. 2 illustrates an example implementation of a disease management system.

FIG. 2 illustrates an example implementation of a disease management system 1103 and applicator 1190 for applying a disease management system 1103 to a patient. Disease management system 1103 can include any one or more of the features discussed above with respect to the disease management system 1101 in addition to the features described below. In the illustrated example, an applicator 1190 may be configured to mate with the disease management system 1103. In some examples, an applicator 1190 may include a safety button 1192 for release or other interaction with the applicator 1190. In the illustrated example, a disease management system 1103 may include one or more LEDs 1160 that may be configured to output information using one or more of color, frequency, and length of display. In some examples, the disease management system 1103 may include a buzzer 1176, haptic actuator 1170, or other feedback mechanism, such as a speaker to output information to the patient, such as an alarm. In some examples, a disease management system 1103 may include a battery 1174, controller 1172. In some examples, a disease management system 1103 may include aspects of a medication administration system, such as a bladder 1180, a bladder pressure applicator 1178 to provide pressure on the bladder (such as a component of a pump), actuator 1182, pump gears 1184, and a pump 1186. In some examples, a disease management system 1103 may include one or more needles 1158 that may include one or more analyte sensors (such as a glucose sensor) 1156. In some examples, a disease management system 1103 may include one or more needles 1162 that may include one or more cannulas 1164 configured to administer medication to the patient. In some examples, a disease management system 1103 may include an air bubble sensor 1152 configured to detect the presence of air bubbles in the medication prior to delivery to the patient. In some examples, a glucose control system 1103 may include one or more physiological sensors 1154, such as a non-invasive physiological sensor including but not limited to a pulse sensor. In some examples, the disease management system 1103 may include a base plate 1106 and an adhesive layer 1168 below the base plate 1106 to provide adhesion of the disease management system 1103 to the patient's skin. As described below, a housing of the disease management system 1103 may consist of a combination of flexible and rigid material so as to both provide support for the components of the disease management system 1103 and allow conforming, at least in part, of the disease management system 1103 to the skin of the patient.

The adhesive layer 1168 may be configured to provide adhesion for a prolonged period. For example, the adhesive layer 1168 may be configured to adhere the disease management system 1103 to the skin of a patient for a period of 1 day, 3 days, 6 days, or more or fewer days or hours. In some examples, the adhesive layer may be configured to have an adhesive force sufficient to prevent accidental removal or movement of the disease management system 1103 during the intended period of use of the disease management system 1103. In some examples, the adhesive layer 1168 may be a single layer of adhesive across at least a portion of a surface the disease management system 1103 that is configured to interface with the patient. In some examples, the adhesive layer 1168 may include a plurality of adhesive areas on a surface of the disease management system 1103 that is configured to interface with the patient. In some examples, the adhesive layer 1168 may be configured to be breathable, adhere to the patient's skin after wetting by humidity or liquids such as tap water, saltwater, and chlorinated water. A thickness of the adhesive may be, for example, in a range of 0.1 to 0.5 mm or in a range of more or less thickness.

In some examples, a needle 1158, 1162 may be inserted at different depths based on a patient age, weight, or other parameter. For example, a depth of insertion of a medication cannula may be approximately 3 mm for 7 to 12 year olds. In another example, a depth of insertion of a medication cannula may be approximately 4 mm for 13 year olds and older. In another example, a depth of insertion of a medication needle may be approximately 4 to 4.5 mm for 7 to 12 year olds. In another example, a depth of insertion of a medication needle may be approximately 5 to 5.5 mm for 13 year olds and older. In another example, a depth of insertion of an analyte sensor may be approximately 3 mm for 7 to 12 year olds. In another example, a depth of insertion of an analyte sensor may be approximately 4 mm for 13 year olds and older. In another example, a depth of insertion for a needle associated with an analyte sensor may be approximately 4 to 4.5 mm for 7 to 12 year olds. In another example, a depth of insertion for a needle associated with an analyte sensor may be approximately 5 to 5.5 mm for 13 year olds and older. However, other values or ranges for any of the inserted components are also possible.

B. Example Muscle Wire Pumps

Figure 3:
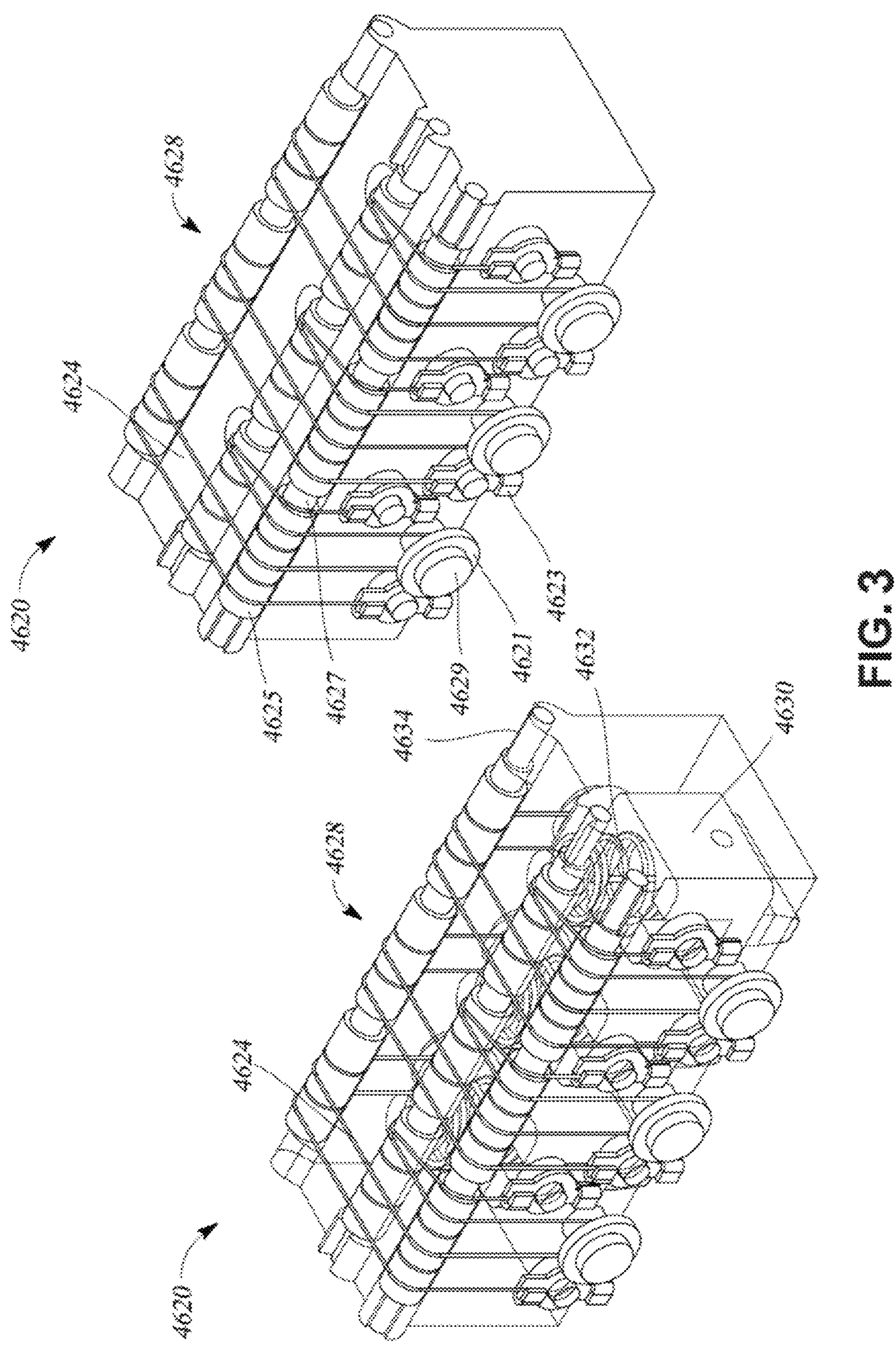
FIG. 3 illustrates perspective views of an example muscle wire pump of a disease management system.

FIG. 3 illustrates aspects of an example blocker style pump using muscle wire. A muscle wire pump may use muscle wire to apply force to tubing or a flow path of medication as a result of interaction between at least a spring and muscle wire.

FIG. 3 illustrates a first configuration of a muscle wire pump making use of rollers. In the illustrated example, muscle wire 4628 may be wrapped around or otherwise in contact with one or more rollers 4625 resting on spacers 4627 on a center cam 4634. The spacers 4627 and center cam 4634 may be located on a top side of the pump assembly. However, other configurations are also possible. Additionally or alternatively, the muscle wire 4628 may be wrapped around one or more rollers 4621 configured to rotate around at least one pin 4629 placed on a side of the pump assembly. However, other configurations are also possible. The muscle wire 4624 may be coupled to one or more blockers 4630, also referred to herein as plungers. The muscle wire 4624 may be configured to receive electrical current through a wire terminal 4623. When powered, the muscle wire 4624 may contract and move with rollers, causing a plunger 4630 to lift. When no power is applied, the muscle wire 4624 may loosen and allow a spring 4632 to push the plunger down onto tubing (not shown). By modifying the power to the muscle wire 4624, the plunger 4630 may squeeze and perform pumping actions on the tubing, facilitating transfer of medication from a pouch to the cannula.

Figure 4:
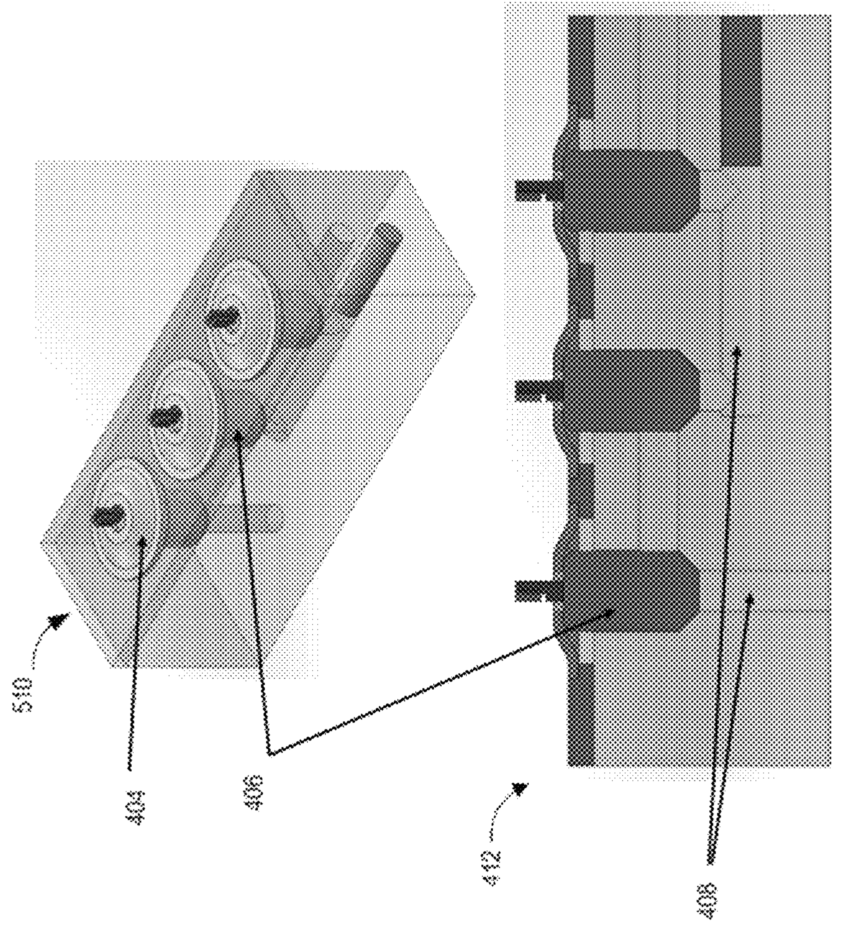
FIG. 4 illustrates example components of another example muscle wire pump of a disease management system.

Components of a muscle wire pump system, such as shown in FIG. 3, may be replaced or simplified in order to, for example, reduce complexity of the pump, improve assembly, lower response time, improve pump speed, and lower the dependence of the pump function on the modulus of elasticity (or Young's modulus) of the tube to achieve desired performance. For example, as illustrated in FIG. 4, one or more helical springs may be replaced with disc springs 404. Additionally or alternatively, the profile and design of one or more plungers 406 may be simplified. Additionally or alternatively, an orientation of the tubing with respect to the one or more plungers may be changed. For example, an orientation of tubing with respect to the plungers may be configured so that a plunger requires less pressure to compress the tubing or otherwise interrupt the flow of medication in the tubing.

As shown in FIG. 4, a spring of a muscle wire pump may include a disc spring 404. In some examples, a disc spring 404 may include silicone or other polymer, such as thermal plastic elastomer (TPE), thermal plastic polyurethane (TPU). Other materials may also be used that are capable of providing a sufficient restoring force in response to displacement of at least a portion of the disc spring to move a plunger of the muscle wire. In some examples, the disc spring may include at least a portion configured to be displaced that has an approximately frusto-conical shape or the like. In some examples, the disc spring may be approximately flat when not displaced. In some examples, the disc spring may be approximately frusto-conical when displaced. Other shapes of the disc spring may also be possible. For example, the disc spring may have an approximately circular top-down profile with a curved side profile. In some examples, the curved side profile may include an S-shaped curve. However, other curves of a curved side profile are also possible.

A plunger 406 can be configured to compress a tube configured to carry medication from a medication pouch to a patient. However, other configurations of a plunger and medication delivery or flow path are also possible. For example, as illustrated in FIG. 4, a plunger 406 may be configured to block a flow path of medication in a tube 408. In some examples, the plunger 406 may be configured to seal or block or at least partially seal or block a portion of the tube or flow path 408. In some examples, the plunger 406 may include a material, such as silicone, configured to form a seal when pressed into the flow path in the tube. The plunger 406 may be overmolded to secure or stabilize the plunger 406. For example, the overmold may include silicone or a material of the like. The plunger 406 may include a seal (e.g., O-ring seal) to maximize the formation of the seal formed when pressed into the flow path. This can minimize the amount of fluid that may escape from the flow path. A shape of the plunger 406 may be any suitable shape to block a flow path directly or indirectly. For example, a plunger 406 may be configured to compress a tube or flow path, directly block a flow path of the medication or the like. In some examples, a contact point of the plunger, such as at least one surface of the plunger 406 configured to engage directly or indirectly with the flow path of the medication, may be rectangular, square, circular, elliptical, oblong, asymmetrical, or symmetrical. A plunger 406 may be configured to be engaged by the one or more springs 404 such that the one or more springs 404 can provide pressure to the plungers 406 in order to block or partially block the flow path. In some examples, the one or more springs 404 may apply a retraction pressure to the plungers 406 to interrupt the flow path. In other words, the springs 404 may retract from the muscle wires to allow the plungers 406 to interrupt the flow path.

Figure 5B:
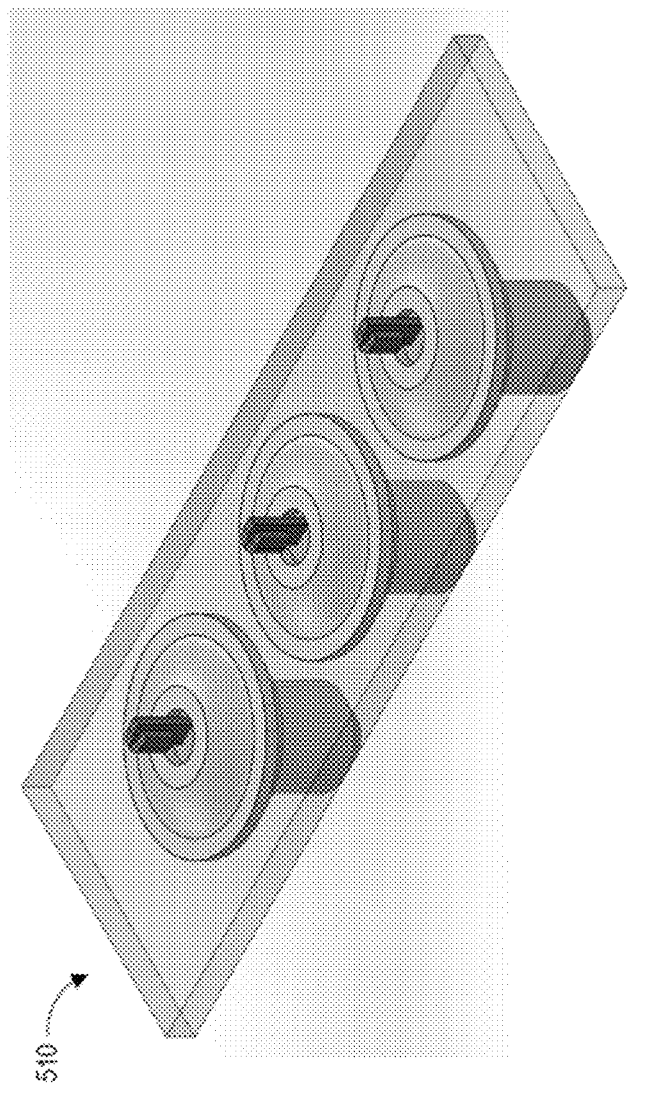
FIGS. 5A, 5B, 5C, and 5D illustrate views of example blocker and silicone membrane, which acts as a spring components of an example muscle wire pump of a disease management system.
Figure 5A:
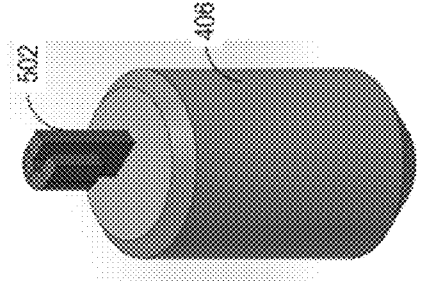

As shown in FIGS. 5A and 5B, in some examples, the plungers 406 may be configured to be engaged by a lifting mechanism through a coupling 502, such as a crimp for a muscle wire configured to contract when an electrical current is applied. The lifting mechanism may lift the plunger from the area of the flow path in order to facilitate flow of medication from the medication pouch to the patient. In some examples, a plunger 406 may include or be coupled to a coupling 502 such as a muscle wire crimp or engagement portion. The muscle wire crimp 502 may be configured to grab or otherwise couple the muscle wire to the plunger, directly or indirectly. While a muscle wire is described herein as the lifting mechanism in many examples, other types of lifting mechanisms may additionally or alternatively be used.

Figure 5D:
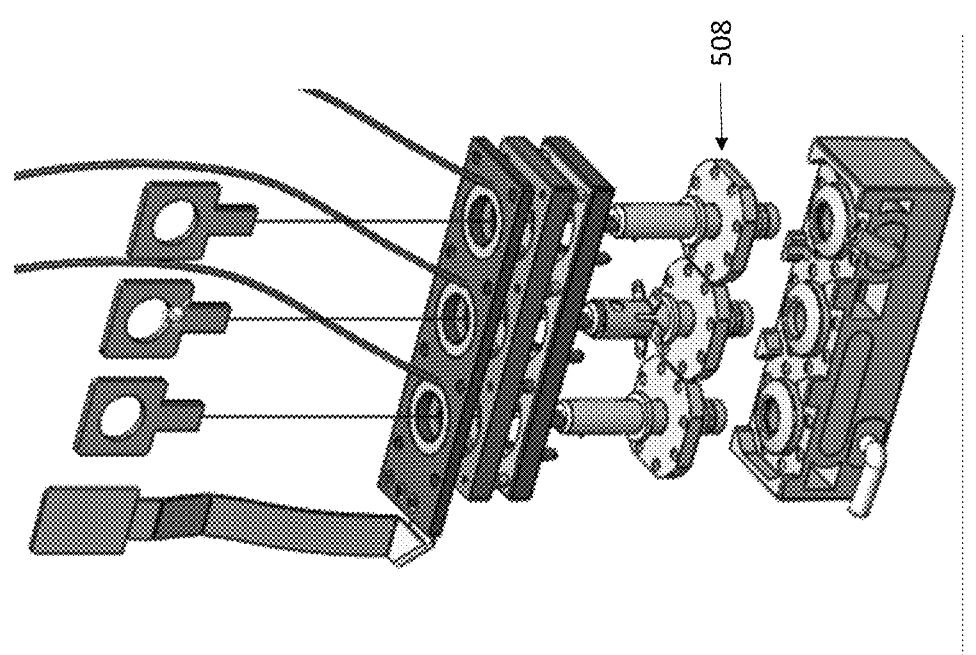
Figure 5C:
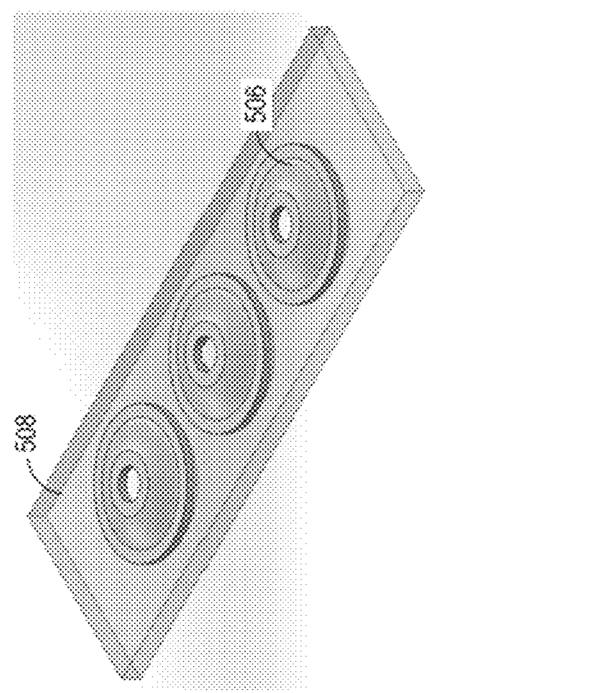

As illustrated in FIGS. 5C and 5D, one or more components of a muscle wire pump may be overmolded and/or chemically bonded together as part of a manufacturing process. For example, one or more springs 404, 506 may be bonded to a plate 508 to form an assembly 510 with the plungers 406, wherein the plate is configured to include holes to allow one or more plungers to move at least a portion of the plunger in a vertical direction with respect to a horizontal plane of the plate 506. The one or more springs 506 can provide a retraction pressure to the plungers 406 to interrupt the flow path. The springs 506 may include a membrane configured to encase the spring. For example, the membrane may include silicon, or a material of the like.

Figure 6:
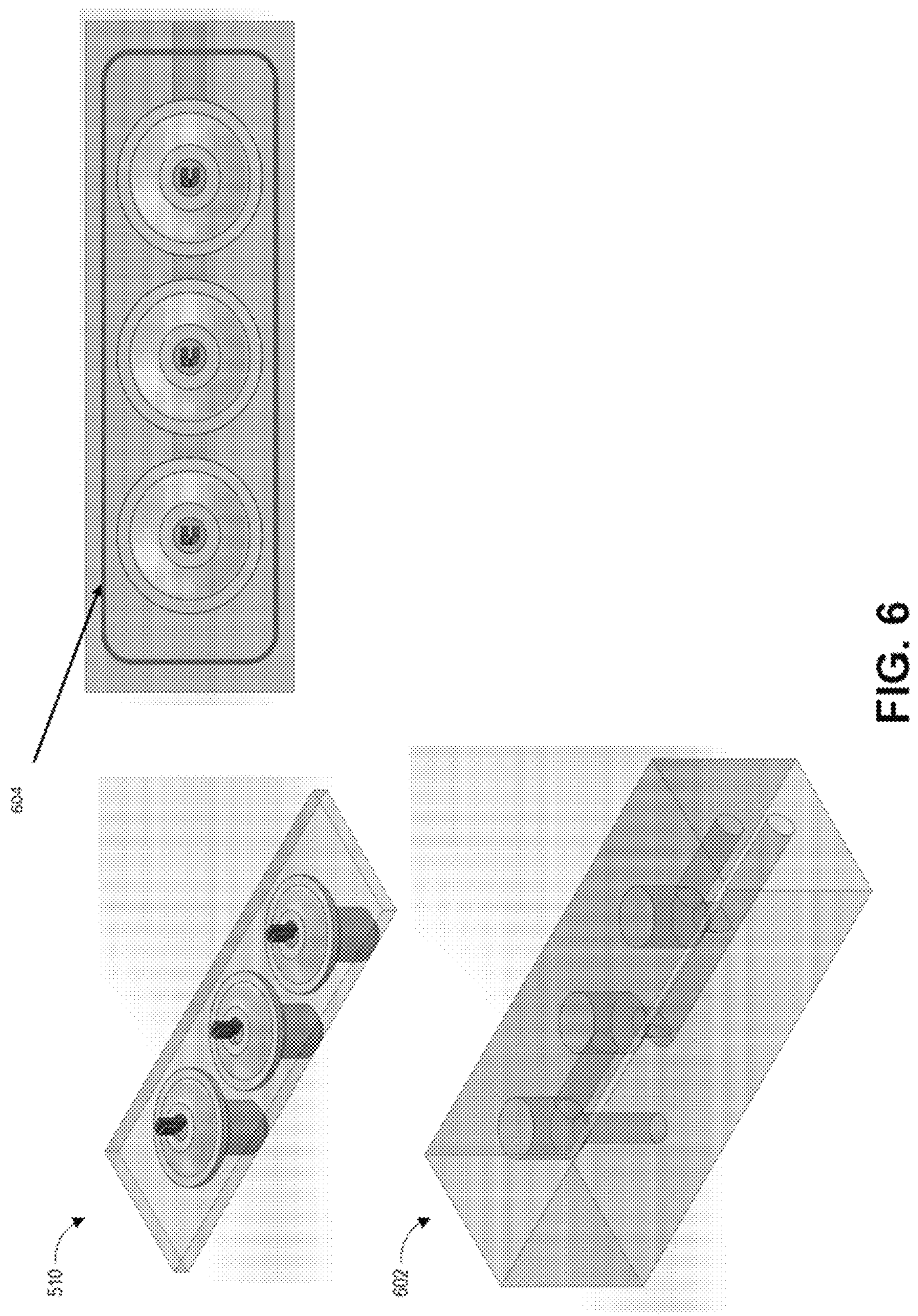
FIG. 6 illustrate views of an example connection of blocker and silicone membrane, which acts as a spring components to an example fluid line of an example muscle wire pump.

As shown in FIG. 6, an assembly 510 may be configured to engage with a bottom portion 602 of a pump that includes the flow path of medication. The assembly 510 may be configured to be welded (for example, laser welded) or otherwise permanently or semi-permanently coupled to the bottom portion 602. As illustrated in FIG. 6, an assembly may be integrated into a larger assembly or configured to couple the pump assembly into a medication delivery device, such as a disease management device illustrated in FIGS. 1-2.

Figure 7A:
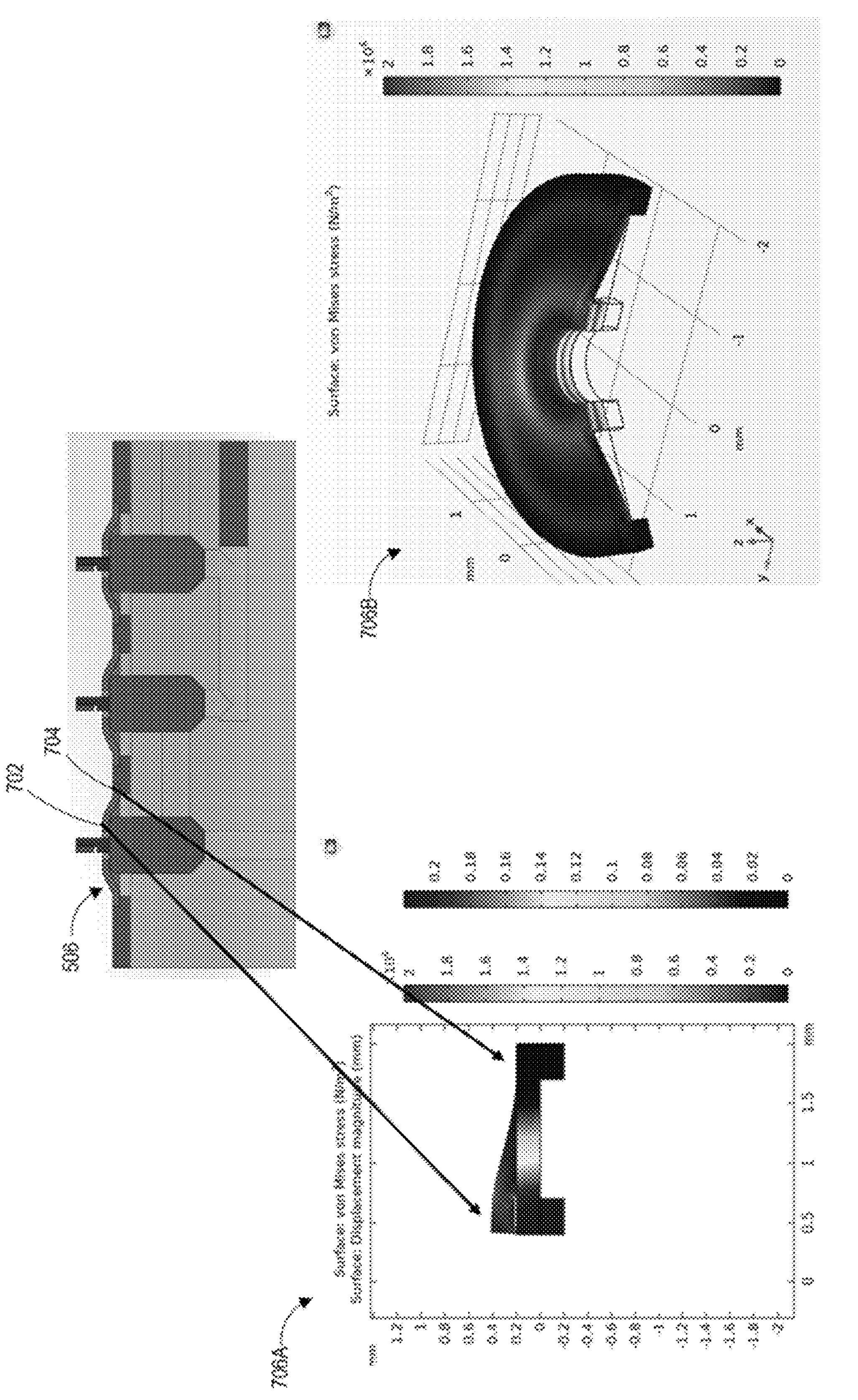
FIGS. 7A, 7B, and 7C illustrates an example functioning of a spring component of an example muscle wire pump.
Figure 7B:
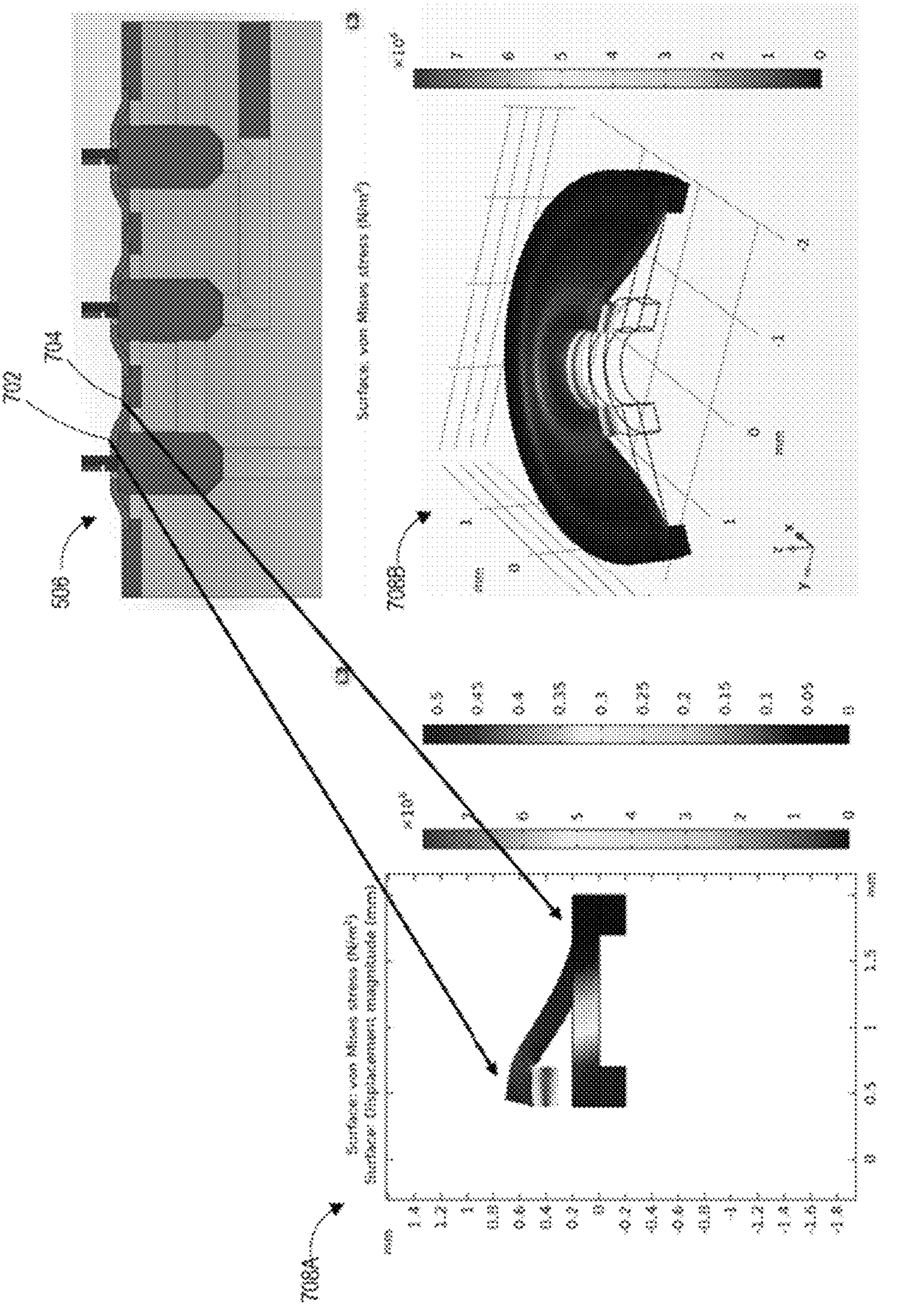
Figure 7C:
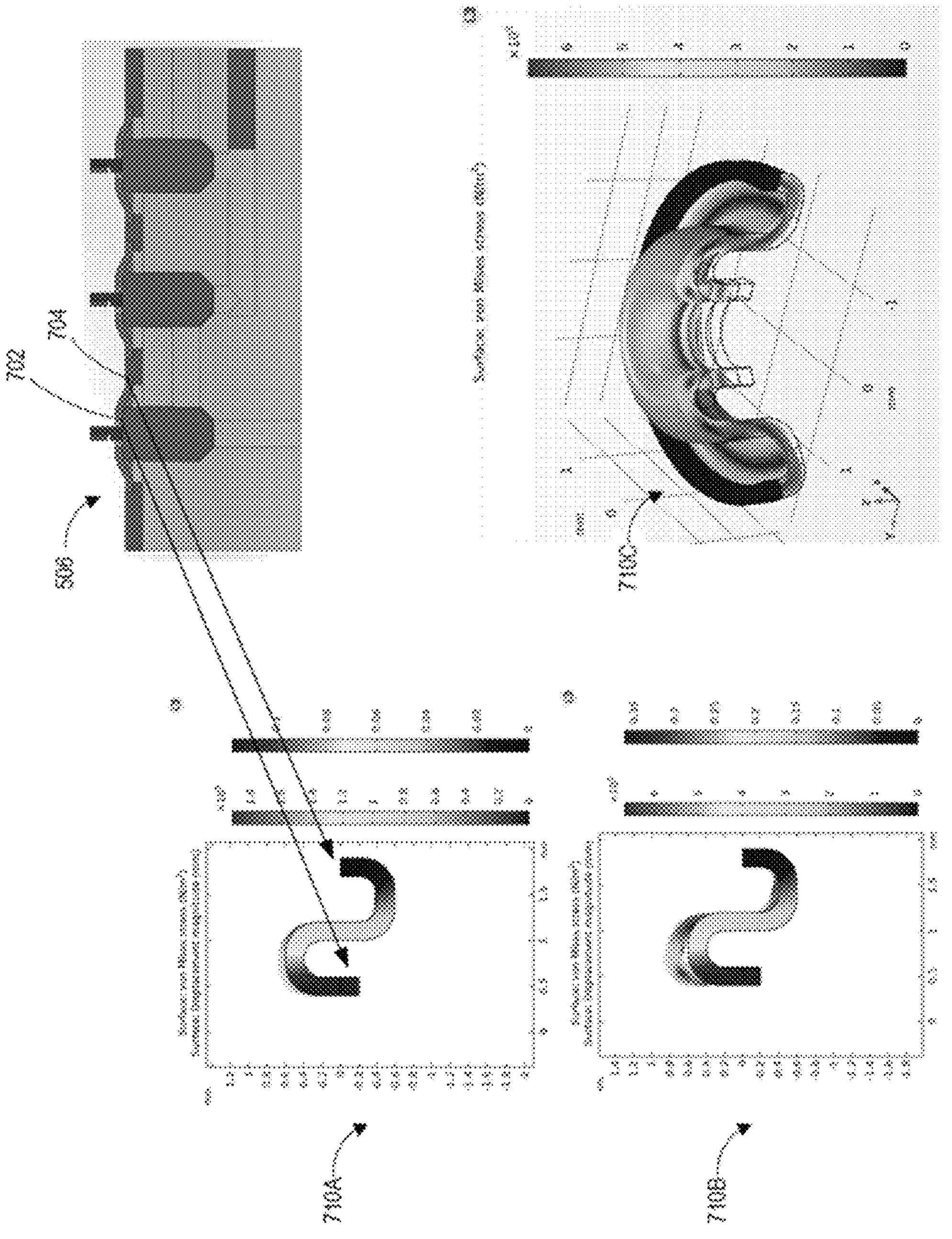

FIGS. 7A-7C illustrate example disc spring shapes and simulations of displacement and force for various disc spring shapes illustrated. In the examples illustrated in FIGS. 7A and 7B, a disc spring comprises an approximately flat or frusto-conical shape. In some examples, the dimension of the disc spring may correspond to a dimension of a tube or diameter of a medication flow path. In some examples, the dimension of the disc spring may correspond to a geometry of a plunger. A force limit for exertion on a disc spring can be calculated based on a pressure limit times the open area of the disc spring. An open area can be calculated as: Open area$=\pi(D^{outer}/2)^2 D^{inner}/2^2$. A pressure limit can be: 300/760 atm or $(4\times10^4)(N/m^2)$.

In an example disc spring with an inner diameter of about 0.0 mm and an outer diameter is about 0.8 mm. A force limit may be calculated as 0.002 kgf. A safe force limit may be some percentage smaller than the total force limit. For example, in the same example, a safety force limit may be 10 gf.

FIG. 7A shows diagrams 706A, 706B illustrating example stress on the surface of a disc spring during displacement of about 0.2 mm of an interior point 702 of the disc spring with respect to an exterior point 704. As shown, stress is greater on the displaced portion of the disc spring and can reach up to $(2\times10^6)(N/m^2)$ or more for a displacement of approximately 0.25 mm.

FIG. 7B shows diagrams 708A, 708B illustrating example stress on the surface of a disc spring during displacement of about 0.5 mm of an interior point 702 of the disc spring with respect to an exterior point 704. As shown, stress is greater on the displaced portion of the disc spring and can reach up to $(8\times10^6)(N/m^2)$ or more for a displacement of 0.5 mm.

FIG. 7C shows diagrams 710A, 710B, 710C illustrating example stress on the surface of a disc spring having an S-shaped curve between an interior point 702 and exterior point 704. Diagram 710A illustrates stress during displacement of about 0.12 mm of an interior point 702 of the disc spring with respect to an exterior point 704. As shown, stress is greater on the displaced portion of the disc spring and can reach up to $(2\times10^6)(N/m^2)$ or more for a displacement of 0.2 mm. Diagram 710B illustrates stress during displacement of about 0.35 mm of an interior point 702 of the disc spring with respect to an exterior point 704. As shown, stress is greater on the displaced portion of the disc spring and can reach up to $(7\times10^6)(N/m^2)$ or more for a displacement of 0.35 mm.

Figure 8:
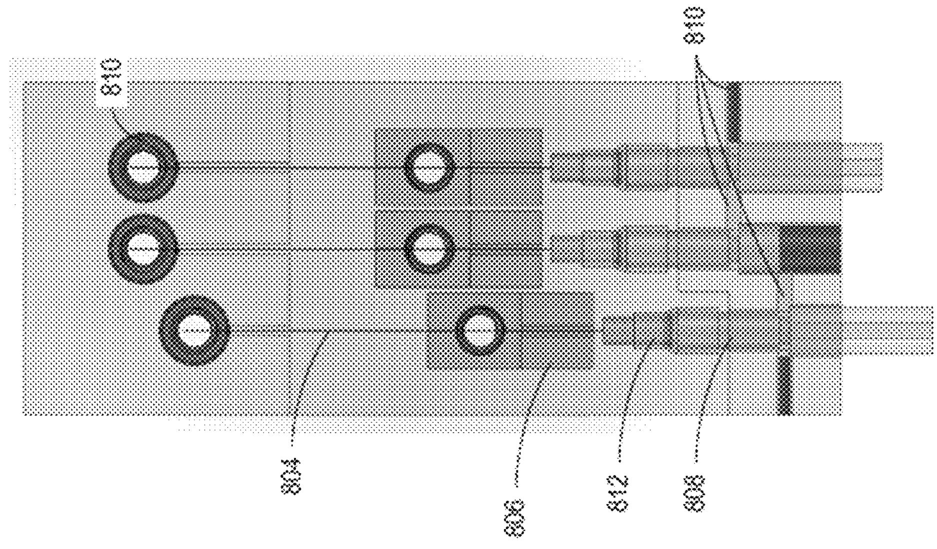
FIG. 8 illustrates example operation of an example muscle wire pump.
Figure 8:
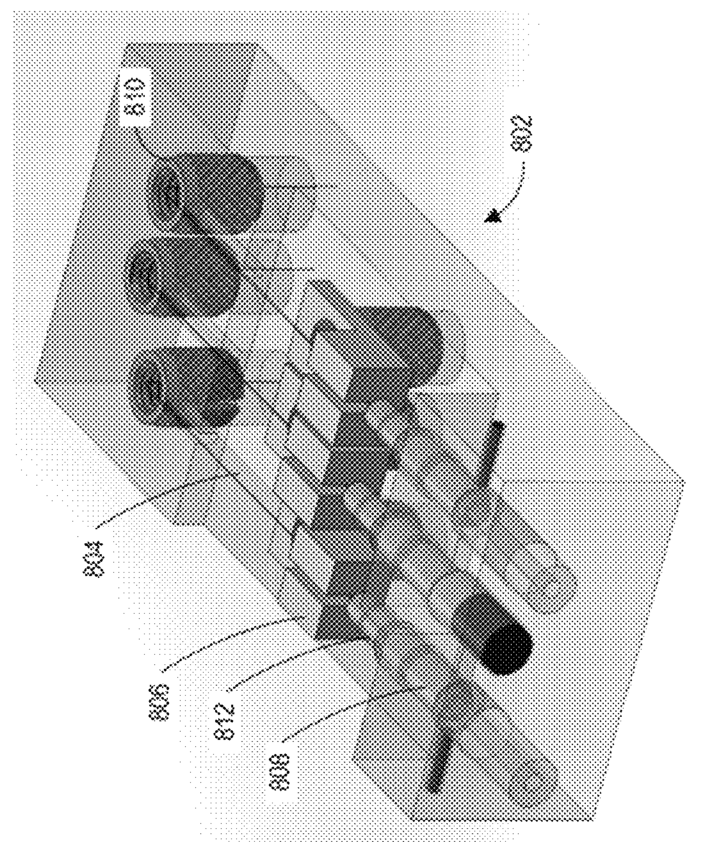

FIG. 8 illustrates an example functioning of an example muscle wire pump 802. In the illustrated example, a muscle wire pump 802 may include a plurality of muscle wires or muscle springs 804, one or more guides 806 for the muscle wires 804, one or more plungers (also referred to herein as pistons) 808, and one or more flow paths 810. More, fewer, and/or different components may also be used.

A pump may include a muscle wire 804 for each plunger 808. The muscle wire 804 may include any material configured to contract when electrical current is applied. For example, a muscle wire 804 may include nitinol or a nickel titanium alloy. Other shape memory alloys may also be used. In some examples, a muscle wire 804 may be suspended so as to maintain tension. In some examples, a guide 806 may be used to aid in support of the wire 804. In some examples, a coupling component 810 may be configured to hold a guide 806, muscle wire 804, or other components in place with respect to the pump or disease management system to which the pump is coupled. Additionally or alternatively, the coupling component 810 may help guide or couple the muscle wire 810 towards or to electronics of the pump configured to apply electrical current to the muscle wire. A muscle wire 804 may be configured to connect to a plunger

808. The plunger 808 may be configured to block, directly or indirectly, a flow path 810 of a medication. The assembly may include a plurality of plungers 808 and muscle wires 804. A spring 812 may be coupled to each plunger 808 to provide force to the plunger 808 in order to block the flow path.

Figure 9:
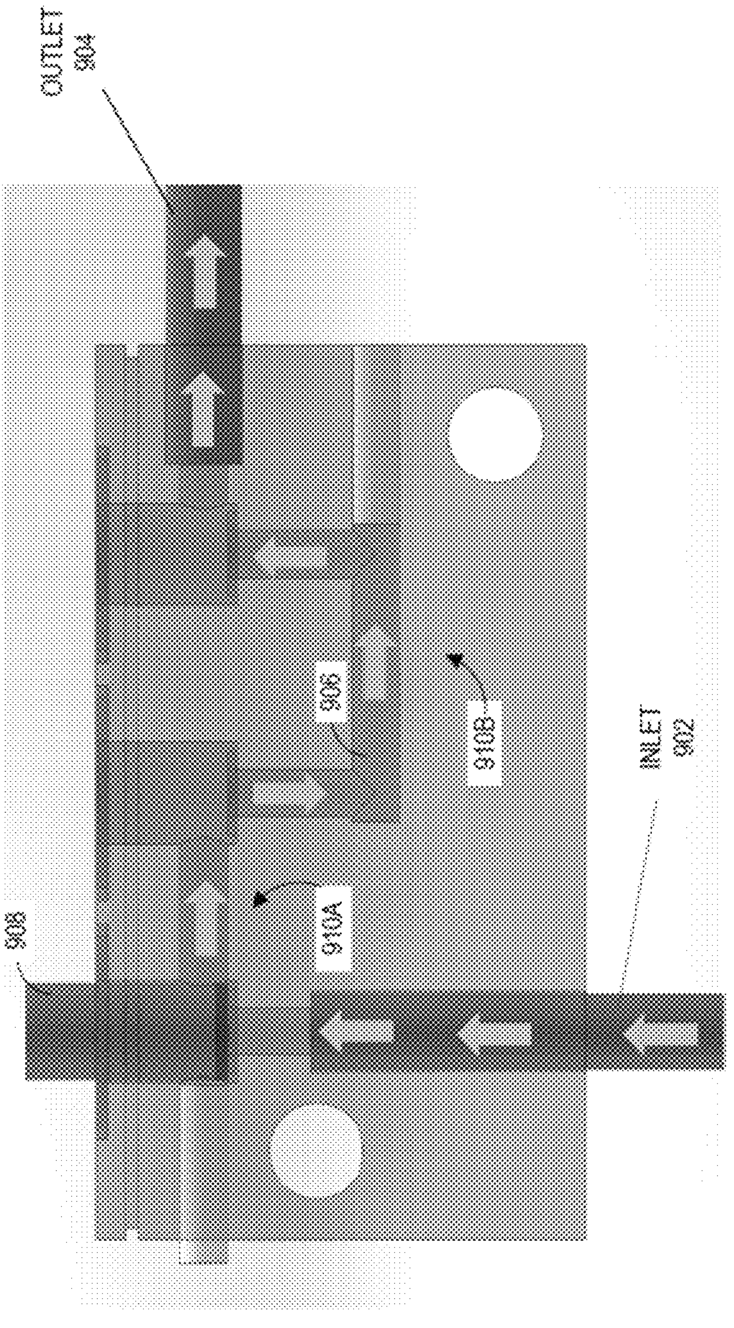
FIG. 9 illustrates an example flow path of a muscle wire pump.

A controller may be configured to control the operation of the pump by operating the plurality of plungers in a sequence. FIG. 9 illustrates an example flow path 906 from an inlet 902, which may be associated with fluid from a medication pouch to an outlet 904, which may be associated with a cannula configured to deliver medication to a patient. The fluid and/or medication pouch can be under pressure. In some examples, the pressure applied to the fluid pouch may be minimal, but can be sufficient to push the fluid into or through the flow path. As fluid leaves the fluid pouch, the pouch can collapse and continue to apply pressure to the fluid. Alternatively, the medication pouch does not need to be under pressure where the plungers are configured to generate negative pressure to pull fluid into the flow path. A plunger, such as a first plunger 908, may be configured to be closed or blocking a flow path 906 in a first configuration. In order to push medication through the inlet 902 to the outlet 904, the controller may open or lift the plunger 908 so that medication flows in an area 910A of the flow path between the first plunger and a second plunger. The first plunger and the second plunger may be lifted approximately simultaneously or at comparable times. The lifting of the first plunger and the second plunger at comparable times can create a vacuum that causes medication to flow into an empty cavity. This can allow medication to flow into the area 910A. The medication can flow into the flow path either by positive pressure applied at the medication pouch or by negative pressure generated by the retraction of each plunger. The controller may close or lower the first plunger to close or block the flow path. Next, the second plunger may be closed or block the flow path at approximately the same time or comparable times as the third plunger is lifted. This can minimize the amount of fluid that may flow back from the patient due to the vacuum formed and also creates positive pressure on the medication in the flow path as the second plunger releases and presses down on the medication. This can also cause the medication to flow from the area 910B between the second plunger towards the outlet 904. In some examples, the closing of the second plunger can be slightly delayed with respect to the contraction of the third plunger. This delay can be accounted for in the timing such that the second plunger may be released before the third plunger is raised so that both plungers move simultaneously or nearly simultaneously. This may be due to the increase in temperature of a muscle wire connected to the second plunger. In some examples, the controller may open and close the first plunger and the second plunger approximately simultaneously and open the second plunger when the first plunger and the third plunger are closed. In performing this sequence, medication may be pumped from the inlet 902 to the outlet 904.

C. Example Feedback Mechanism

Figure 10:
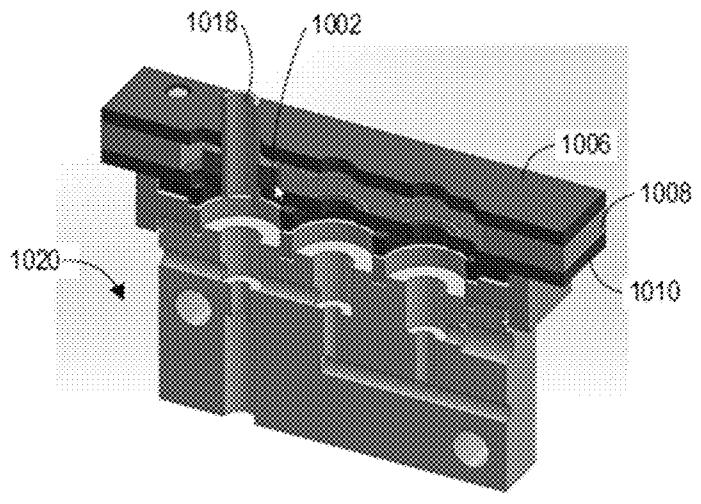
FIG. 10 illustrates an example feedback control system that may be part of a muscle wire pump.
Figure 10:
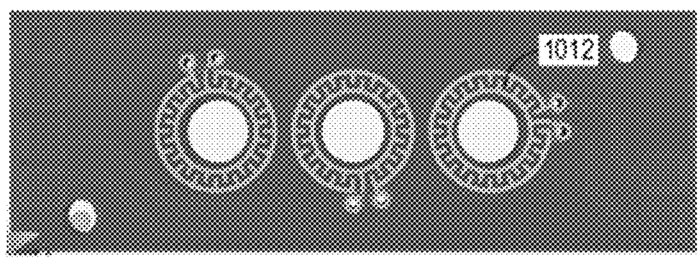
Figure 10:
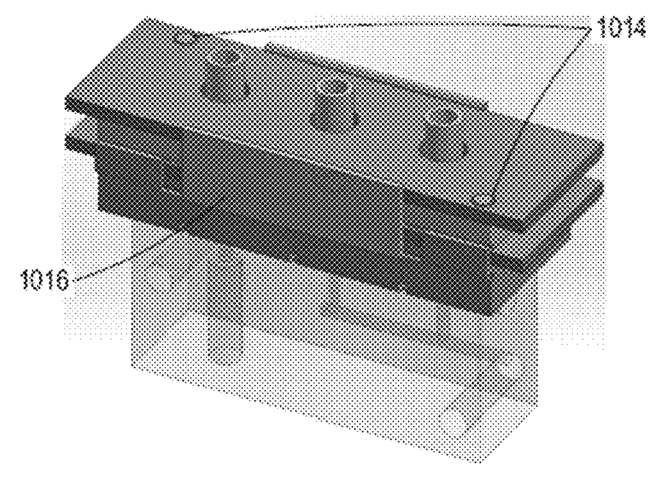
Figure 12:
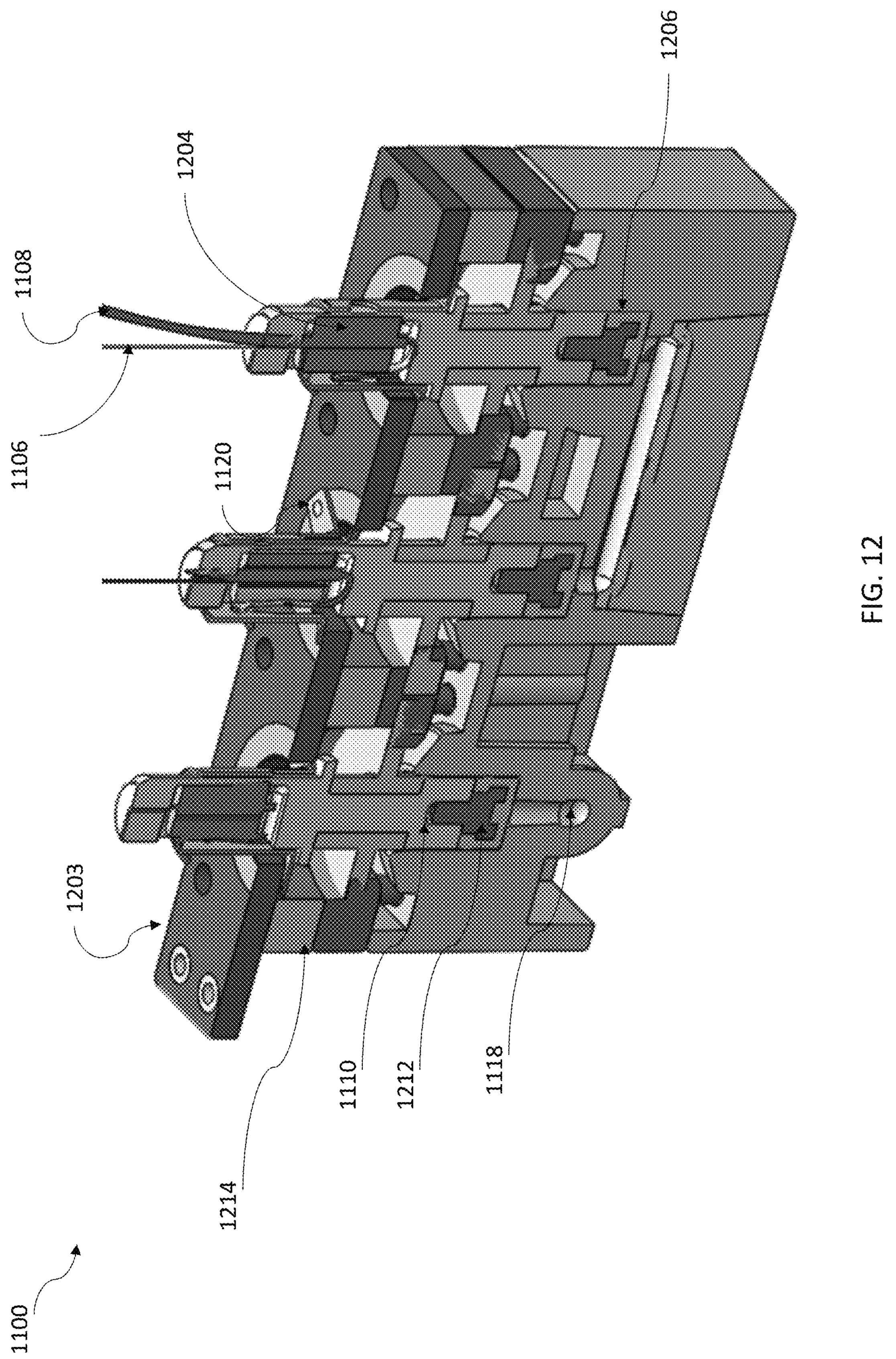
FIG. 12 illustrates an example muscle wire pump.

In some examples, a pump system can include a feedback control system. FIG. 10-FIG. 12 illustrate example aspects of feedback control for an example pump system. As illustrated in FIG. 10, a feedback mechanism may include, but is not limited to, a top feedback PCB 1006, a bottom feedback PCB 1010, one or more contact rings 1002 (mounted to the blocker or plunger 1018) and one or more spacers 1008 to mount PCBs. During assembly, the bottom feedback PCB 1010 may be mounted to the main housing 1020 first. Other components may then be assembled layer by layer on top of the bottom feedback PCB 1010. One or more components of the feedback system can be held in place and aligned using one or more components, such as alignment pins 1014 and one or more latches 1016. For example, a top PCB 1006 and bottom PCB may be aligned and held in place using the alignment pins 1014 and one or more latches 1016. A pump housing 1020 may be made with a plastic, such as a COC or PP material. It is also possible that the housing is made with other plastic polymer, including but not limited to HDPE with $SiO_2$ coating. A contact ring 1002 may be made with a high conductive material. The contact ring 1002 can be coated with carbon filled polymer or electrically conductive silicone. A pattern and/or layout of the feedback PCB can play an important role. A pattern can significantly enhance the detection when the contact ring shorts the circuit. An example pattern 1012 is illustrated in FIG. 10.

The pump may include feedback notification to a controller when the plungers have traveled a desired distance so as not to damage the shape memory alloy (such as a disc spring) by over stretching it. The feedback can also give better control of bolus delivery by tightly controlling the plunger travel distance. The feedback control signals may additionally or alternatively indicate when the plunger is fully seated and hence, blocking fluid flow. The feedback control signals may additionally or alternatively indicated when the plunger is fully open and hence, allowing fluid flow. A feedback control may occur based on a short created by the plunger between two traces on a printed circuit board 1006, 1010 that is located above or below the plunger. The printed circuit boards may include one or more contact rings 1002 configured to detect contact by the plunger. One or more spacers 1008 between the circuit boards may prevent accidental or unintended shorts. The controller reads the feedback control signal and when it detects a short circuit, the controller can disable the plunger from moving any further.

When a top feedback PCB 1006 detects that plunger 1018 moves to the top position, the plunger may be held in place. Pulse width modulation (PWM) can be activated, which maintains the temperature in the muscle wire. Accordingly, the muscle wire can stay stationary and hold the plunger stationary. Thus, the muscle wire may not pull with additional strain or relax in any strain. Additionally or alternatively, when the top feedback PCB 1006 detects that plunger 1018 moves to a top position, it will cut down the power for the muscle wire. When the top feedback detects the plunger is disengaged, it can power up again. This back-and-forth power cycle will allow the plunger to stay near the top position. When the bottom feedback PCB detects the plunger touches the bottom, the system knows that the plunger is fully closed. This can ensure the plunger is fully closed.

FIG. 11 illustrates an example of a muscle wire pump 1100 that includes a feedback mechanism 1102. The feedback mechanism 1102 may work in combination with other components of the muscle wire pump to maximize control, accuracy, precision, etc. of the muscle wire pump. For example, the muscle wire pump 1100 can include a plurality of electrical connectors 1104, a plurality of muscle wires 1106, and a plurality of conductive wires configured to connect to the muscle wire 1108. The electrical connector 1104 and conductive wire 1108 may be used to promote or allow a signal to be sent to the lifting mechanism or muscle wires 1106. As described above, the muscle wire pump can include a plurality of plungers 1110, a pump lid 1112, a pump housing 1114, a pump outlet 1116, and a pump inlet 1118. The muscle wire pump 1100 can further include at least one feedback ring 1120 that may allow the feedback mechanism 1102 to monitor the position and status of each plunger 1110. In some examples, there can be a feedback ring connected to each plunger within the muscle wire pump. For example, the feedback ring 1120 can allow the feedback mechanism to have a signal that promotes monitoring or controlling the status of each of the plungers 1110. In some examples, when the plunger is in an open position, the feedback ring can contact the feedback mechanism which may trigger a signal sent to the feedback mechanism. The signal may allow the feedback mechanism to know the plunger is in an open position. In some examples, when the plunger is in a closed position, the feedback ring can contact the feedback mechanism which may trigger a signal sent to the feedback mechanism. The signal may allow the feedback mechanism to know the plunger is in a closed position. In some examples, when the feedback ring is not in contact with the feedback mechanism, the feedback mechanism may not monitor the position and status of the plunger. The muscle wire pump 1100 can also include a cable (e.g., a flex cable) configured to connect to the feedback mechanism 1102.

FIG. 12 illustrates a cross-section view of FIG. 11 The integration, connection, and/or coupling of each component of the muscle wire pump can be important to the feedback mechanism. As shown in FIG. 12, the muscle wire pump 1100 can include a feedback ring 1120 connected to each one of a plurality of plungers 1110, a PCB 1203, a crimp connector 1204, at least one conductive wire 1108, a seal 1206, at least one muscle wire 1106, an inlet 1118, an adapter 1212 configured to connect to the plunger 1210, and a spacer 1214. The feedback ring 1120 can be configured to directly contact the PCB 1203. The crimp connector 1204 may be configured to couple each conductive wire each muscle wire for each of the plurality of plungers within the muscle wire pump. Accordingly, this contact can trigger the feedback mechanism to monitor or control the position and status of the plungers 1110. The direct contact between the feedback ring 1120 and the PCB 1203 can be useful in allowing the feedback mechanism to have a signal that promotes monitoring or controlling the status of the plunger 1110. For example, the signal may allow the feedback mechanism to determine the position of the plunger. In some examples, the signal may allow the feedback mechanism to determine whether the plunger is in an open or closed position. The feedback ring 1120 can maximize control, accuracy, precision, etc. of the muscle wire pump. In some examples, as the conductive wire 1108 (for example, a copper wire) continues the electrical connection to the muscle wire pump, including the crimp connector 1204, the conductive wire 1108 can be connected to both the muscle wire 1106 and the feedback ring 1120. This connection can allow the feedback mechanism to monitor the position and/or status of the plungers upon the feedback ring 1120 contacting the PCB 1203 to trigger a signal. Specifically, as shown in FIG. 12, the conductive wire 1108 can exit an internal compartment of each of the plurality of plungers at an exit point at which the feedback ring 1120 is connected to each of the plurality of plungers 1110. This can allow for the conductive wire 1108 to connect to both the muscle wire 1108 and the feedback ring 1120.

The feedback mechanism allows a controller to know the position of the plungers. A feedback signal can be used to allow the controller to know whether the plunger is in an open or closed position. In some examples, a feedback signal can be used to allow the controller to know whether the partially or fully open the plunger. For example, a controller may open a plunger 25, 50, 75 or at 100% open position. The level of opening of the plunger can in turn control the bolus amount or amount of fluid pumped through the pump system. Similarly, the level of opening of the plunger can determine the rate at which the fluid flows through the pump system because the level of opening of the plunger can determine the volume of the fluid. Advantageously, this can save power in cases where at least some of the plungers do not need to be fully opened to deliver a sufficient bolus. This may vary based on the rate that may be necessary to pump the patient specific bolus amount through the pump system. Additionally, or alternatively, stopping the power of at least some of the plungers can increase the accuracy of the muscle wire pump system. The plungers may be specifically timed so that fluid can move from one direction to the other, such as from a medication bladder or pouch towards a catheter or cannula embedded in a patient. In some examples, the timing of the plungers can be used to determine the position each of the plurality of plungers. The plungers may each be in an open position at the same time, which may allow an unrestricted flow of fluid from the pouch. The pouch can be pressurized or be under pressure. The pressure from the pouch can cause the medication to flow past the plungers, when the plungers are in an open position. This can be advantageous in ensuring medication is delivered to the patient when it is needed because medication may be released only upon the plungers opening to a level of an open position. Additionally or alternatively, the feedback mechanism may be used such that accurate timing of plunger operation can be implemented. For example, a signal may trigger the feedback mechanism upon a plunger reaching an opening position. In some examples, a signal may trigger the feedback mechanism upon a plunger reaching a closed position. In this manner, the amount of medication delivered to the patient can be controlled because only a small portion of the medication is released at any given time due to the offset timing of the plunger openings.

A controlled amount of medication delivered to the patient can be precise and accurate to the dosage of medication needed. Advantageously, the arrangement, timing or level of opening of the plungers can be finely tuned, which allows for a controlled and/or precise amount of medication to be delivered to the patient. For example, when the plunger is at a 100% open position, the maximum amount of medication is allowed into the muscle wire pump. Similarly, when the plunger is at a position that is less than 100% open, no more than a medication amount equivalent to the open position of the plunger percentage will be delivered to the patient. The feedback mechanism can signal to accurately notify that the correct amount of medication or fluid may be delivered to the patient based on the signal formed when each of the plungers reaches an open position or closed position. Additionally or alternatively, the feedback mechanism can ensure medication does not disperse through the muscle wire pump system.

Advantageously, the feedback mechanism can also provide a safety factor to the muscle wire pump system. For example, the feedback mechanism can recognize or register when the plunger is in an open position and/or when the plunger is a closed position.

D. Terminology

While the above description has pointed out novel features of the invention as applied to various aspects, the skilled person will understand that various omissions, substitutions, and changes in the form and details of the device or process illustrated may be made without departing from the scope of the invention. Therefore, the scope of the invention is defined by the appended claims rather than by the foregoing description. All variations coming within the meaning and range of equivalency of the claims are embraced within their scope.

Reference throughout this specification to "some aspects" or "an aspect" means that a particular feature, structure or characteristic described in connection with the aspect is included in at least some aspects. Thus, appearances of the phrases "in some aspects" or "in an aspect" in various places throughout this specification are not necessarily all referring to the same aspect and may refer to one or more of the same or different aspects. Furthermore, the particular features, structures or characteristics can be combined in any suitable manner, as would be apparent to one of ordinary skill in the art from this disclosure, in one or more aspects.

As used in this application, the terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Similarly, it should be appreciated that in the above description of aspects, various features are sometimes grouped together in a single aspect, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Rather, inventive aspects lie in a combination of fewer than all features of any single foregoing disclosed aspect.

Aspects of the disclosed systems and methods can be used and/or implemented with local and/or remote devices, components, and/or modules. The term "remote" may include devices, components, and/or modules not stored locally, for example, not accessible via a local bus. Thus, a remote device may include a device which is physically located in the same room and connected via a device such as a switch or a local area network. In other situations, a remote device may also be located in a separate geographic area, such as, for example, in a different location, building, city, country, and so forth.

Although described in the illustrative context of certain preferred aspects and examples, it will be understood by those skilled in the art that the disclosure extends beyond the specifically described aspects to other alternative aspects and/or uses and obvious modifications and equivalents. Thus, it is intended that the scope of the claims which follow should not be limited by the particular aspects described above.

What is claimed is:

1. A method to pump liquid medication from a liquid medication reservoir to a patient through a cannula or needle inserted into a patient, the method comprising:

contracting one or more of a plurality of plungers from an uncontracted position to cause a negative pressure to draw medication into a flow path from the liquid medication reservoir, wherein an output of a first plunger of the plurality of plungers is in fluid communication with an input of a second plunger of the plurality of plungers; and retracting the one or more of a plurality of plungers to the uncontracted position by applying a retraction force, wherein the retraction force causes a positive pressure to the medication in the flow path to move medication downstream within the flow path.

2. The method of claim 1, wherein the retracting is performed by providing retraction pressure by a plurality of springs, each of the plurality of springs configured to cause one of the plurality of plungers to return an uncontracted position.

3. The method of claim 2, wherein each of the plurality of springs includes silicon.

4. The method of claim 2, wherein each of the plurality of springs is a disc spring.

5. The method of claim 1, further comprising sensing one or more physiological parameters of the patient with an analyte sensor.

6. The method of claim 1, wherein the liquid medication includes at least one of insulin or glucagon.

7. The method of claim 1, wherein contracting the one or more of the plurality of plungers comprises actuating one or more muscle wires to contract the one or more of the plurality of plungers, each of the one or more muscle wires corresponding to one of the one or more plungers.

8. The method of claim 7, wherein the one or more muscle wires include nitinol wire.

9. The method of claim 1, wherein the plurality of plungers further comprises a third plunger, wherein an output of the second plunger of the plurality of plungers is in fluid communication with an input of the third plunger of the plurality of plungers.

10. The method of claim 7 further comprising one or more hardware processors causing one or more muscle wires to engage the first plunger, the second plunger, and the third plunger in a pattern to cause the liquid medication to flow from the liquid medication reservoir to the patient.

11. The method of claim 10, further comprising:

applying an electrical signal to a first wire and a second wire to cause the first wire to cause the first plunger to open the flow path and create negative pressure to cause medication to flow into the flow path in a first portion and the second wire to cause the second plunger to open the flow path in a second portion;

ceasing applying the electrical signal to the first wire in order to allow a first spring to apply retraction pressure to the first plunger such that the first plunger is retracted to an uncontracted position and causes positive pressure to be applied to the medication in the first portion; and applying a second electrical signal to a third wire to cause the third plunger to open the flow path in a third portion, and ceasing applying the electrical signal to the second wire in order to allow a second spring to apply retraction pressure to the second plunger, such that the second plunger is retracted to an uncontracted position and applies positive pressure to the medication in the flow path in the second portion.

12. A method to engage a system of plungers configured to pump liquid medication through a flow path from a medication reservoir to a patient to a cannula or needle inserted into a patient, the method comprising:

applying a first electrical signal to a first wire and a second electrical signal to a second wire to cause the first wire to contract a first plunger, applying a negative pressure within the flow path in a first portion, and to contract a second plunger to apply a negative pressure within the flow path in a second portion substantially simultaneously to cause flow of the liquid medication, wherein an output of the first portion is in fluid communication with an input of the second portion;

ceasing applying the electrical signal to the first wire in order to allow application of retraction pressure to the first plunger such that the first plunger is retracted to an uncontracted position to apply a positive pressure in the first portion;

applying a third electrical signal to a third wire to contract a third plunger, applying a positive pressure within the flow path in a third portion, wherein an output of the second portion is in fluid communication with an input of the third portion; and ceasing applying the electrical signal to the second wire substantially simultaneously to applying the third electrical signal, application of retraction pressure to the second plunger such that the second plunger is retracted to an uncontracted position and to apply a negative pressure within the flow path in the second portion.

13. The method of claim 12, wherein the retraction pressure is applied using a plurality of springs.

14. The method of claim 13, wherein each of the plurality of springs is a disc spring.

15. A muscle wire pump system configured to manage a liquid medication flow path from a medication reservoir to a patient through a cannula or needle inserted into a patient, the system comprising:

a controller configured to control operation of a pump by operating a plurality of plungers within the liquid medication flow path, wherein an output of a first plunger of the plurality of plungers is in fluid communication with an input of a second plunger of the plurality of plungers;

a plurality of muscle wires each coupled to one of the plurality of plungers, each of the plurality of muscle wires configured to receive an electrical signal and cause contraction of the corresponding plunger, thereby creating a negative pressure to draw medication along the flow path; and a plurality of means for opposing contraction of the plurality of muscle wires, each of the plurality of means for opposing contraction configured to return one of the plurality of plungers to an uncontracted position upon cessation of the electrical signal to the muscle wire coupled to the plunger.

16. The muscle wire pump system of claim 15, wherein the plurality of means for opposing contraction are coupled to a plate forming an assembly with the plurality of plungers.

17. The muscle wire pump system of claim 16, wherein the plate includes one or more holes configured to allow the one or more holes to receive at least a portion of one of the plurality of plungers.

18. The muscle wire pump system of claim 15, wherein the plurality of means for opposing contraction comprise a plurality of springs.

19. The muscle wire pump system of claim 18, wherein the plurality of springs comprise disc springs.

* * * * *